United States Patent
Tornai et al.

(10) Patent No.: US 7,609,808 B2
(45) Date of Patent: Oct. 27, 2009

(54) APPLICATION SPECIFIC EMISSION AND TRANSMISSION TOMOGRAPHY

(75) Inventors: Martin P. Tornai, Carrboro, NC (US); James E. Bowsher, Durham, NC (US); Joerg Peter, Heidelberg (DE)

(73) Assignee: Duke University, Durham, NC (US)

( * ) Notice: Subject to any disclaimer, the term of this patent is extended or adjusted under 35 U.S.C. 154(b) by 715 days.

(21) Appl. No.: 10/106,393

(22) Filed: Mar. 27, 2002

(65) Prior Publication Data

US 2002/0143249 A1    Oct. 3, 2002

Related U.S. Application Data

(60) Provisional application No. 60/279,660, filed on Mar. 30, 2001, provisional application No. 60/283,383, filed on Apr. 13, 2001.

(51) Int. Cl.
*G01N 23/04* (2006.01)
(52) U.S. Cl. .................. 378/63; 600/425; 600/427; 600/436; 378/37; 378/40
(58) Field of Classification Search ............... 600/407, 600/425, 427, 429, 436; 606/130; 250/363.02, 250/363.03, 363.04, 363.05, 269.3, 269.7, 250/370.09; 378/37, 40, 63, 13
See application file for complete search history.

(56) References Cited

U.S. PATENT DOCUMENTS

| | | | |
|---|---|---|---|
| 4,015,836 A * | 4/1977 | Redington et al. | 5/601 |
| 4,220,861 A | 9/1980 | Colombo et al. | |
| 4,426,578 A | 1/1984 | Bradcovich et al. | |
| 4,590,378 A | 5/1986 | Platz | |

(Continued)

FOREIGN PATENT DOCUMENTS

DE    198 55 213    11/1998

(Continued)

OTHER PUBLICATIONS

CJ Thompson, K Murthy, IN Weinberg, F Mako. 1994. "Feasibility Study for Positron Emission Mammography." *Med. Phys.* 21(4):529-538.

(Continued)

*Primary Examiner*—Brian Casler
*Assistant Examiner*—Amanda L. Lauritzen
(74) *Attorney, Agent, or Firm*—Nixon & Vanderhye, PC

(57) ABSTRACT

A compact and mobile gantry for 3-dimensional Application Specific Emission and/or Transmission Tomography (ASETT) imaging of the breast in single photon or coincidence emission modes, and single photon, or coincidence, or x-ray transmission modes. While the ASETT gantry was designed, built and evaluated for imaging metabolically active lesions in the pendant breast, it can also be used to image other organs and objects. This system overcomes physical constraints associated with imaging a pendulous breast in prone patients, while simultaneously satisfying sampling criteria for sufficient data collection in the pendulous breast reference frame. When combined with an offset cone-beam tomographic x-ray transmission imaging system, this dual modality ASETT system could provide simultaneous and coregistered structural and functional information about large or dense breasts, breasts with indeterminate x-ray mammography, and could also be used to accurately 3-dimensionally guide biopsy or surgical resection. Moreover, with the offset beam orientation, the transmission system is designed to have a variable FOV and minimize overall absorbed breast dose.

36 Claims, 13 Drawing Sheets

U.S. PATENT DOCUMENTS

| | | | |
|---|---|---|---|
| 4,649,277 A | | 3/1987 | Terra et al. |
| 5,086,447 A | * | 2/1992 | Siczek et al. ............... 378/197 |
| 5,278,416 A | | 1/1994 | Pierfitte |
| 5,289,520 A | * | 2/1994 | Pellegrino et al. ............ 378/37 |
| D345,606 S | | 3/1994 | Perusek |
| 5,365,069 A | | 11/1994 | Eisen et al. |
| 5,367,169 A | | 11/1994 | Pierfitte et al. |
| 5,409,497 A | * | 4/1995 | Siczek et al. ............... 600/407 |
| 5,415,169 A | * | 5/1995 | Siczek et al. ............... 600/427 |
| 5,451,789 A | | 9/1995 | Wong et al. |
| 5,554,848 A | | 9/1996 | Hermony et al. |
| 5,587,585 A | | 12/1996 | Eisen et al. |
| 5,594,251 A | | 1/1997 | Fleury et al. |
| 5,609,152 A | * | 3/1997 | Pellegrino et al. ........... 600/429 |
| 5,670,783 A | | 9/1997 | Ray |
| 5,757,006 A | | 5/1998 | DeVito et al. |
| 5,760,402 A | * | 6/1998 | Hug et al. ............... 250/363.05 |
| 5,825,031 A | * | 10/1998 | Wong et al. ............ 250/363.03 |
| 5,939,724 A | | 8/1999 | Eisen et al. |
| 5,961,457 A | | 10/1999 | Raylman et al. |
| 6,150,662 A | * | 11/2000 | Hug et al. ............... 250/363.05 |
| 6,200,024 B1 | | 3/2001 | Negrelli |
| 6,298,114 B1 | * | 10/2001 | Yoda ........................... 378/37 |
| 6,435,715 B1 | | 8/2002 | Betz et al. |
| 6,463,122 B1 | * | 10/2002 | Moore ......................... 378/65 |
| 6,545,280 B2 | * | 4/2003 | Weinberg ............... 250/363.02 |
| 6,794,653 B2 | * | 9/2004 | Wainer et al. ........... 250/363.01 |
| 7,254,851 B2 | * | 8/2007 | Salit et al. ....................... 5/601 |
| 2004/0068180 A1 | * | 4/2004 | Collins et al. ............... 600/425 |
| 2007/0064867 A1 | * | 3/2007 | Hansen et al. ................ 378/37 |
| 2007/0176106 A1 | * | 8/2007 | Hefetz .................... 250/363.02 |

FOREIGN PATENT DOCUMENTS

| | | |
|---|---|---|
| EP | 1 004 271 | 11/1999 |
| WO | WO 98/16852 | 4/1998 |

OTHER PUBLICATIONS

G Hutchins, A Simon. 1995. "Evaluation of Prototype Geometries for Breast Imaging with PET Radiopharmaceuticals." *J. Nucl. Med.* 36(5):69P (Abstract).

WW Moses, T Budinger, R Huesman, S Derenzo. 1995. "PET Camera Designs for Imaging Breast Cancer and Axillary Node Involvement." *J. Nucl. Med.* 36(5):69P (Abstract).

CJ Thompson, K Murthy, Y Picard, IN Weinberg, R Mako. 1995. "Positron Emission Mammography (PEM): A Promising Technique for Detecting Breast Cancer." *IEEE Trans. Nucl. Sci.* NS-42(4):1012-1017.

I. Weinberg, S Majewski, A Weisenberger, A Markowitz, L Aloj, L Majewski, D Danforth, J Mulshine, K Cowan, J Zujewski, C Chow, E Jones, V Chang, W Berg, J Frank. 1996. "Preliminary Results for Positron Emission Mammography: Real-Time Functional Breast Imaging in a Conventional Mammography Gantry." *Eur. J. Nucl. Med.* 23(7):804-806.

R Freifelder, J Karp. 1997. "Dedicated PET Scanners for Breast Imaging." *Phys. Med. Biol.* 42:2463-2480.

NK Doshi, Y Shao, RW Silverman, SR Cherry. 2000. "Design and Evaluation of an LSO PET Detector for Breast Cancer Imaging." *Med. Phys.* 27(7):1535-1543.

J Li, C Scarfone, RJ Jaszczak, H Wang, RE Coleman. 1996. Limited angular view MLEM pinhole SPECT for breast tumor detection. *J Nucl Med.* 37(5):214P. (Abstract).

C Scarfone, RJ Jaszczak, J Li, Ms Soo, MF Smith, KL Greer, RE Coleman. 1997. Breast tumor imaging using incomplete orbit pinhole SPET: a phantom study. *Nuc Med Commun.* 18:1077-1086.

H Wang, C Scarfone, KL Greer, RE Coleman, RJ Jaszczak. 1997. Prone breast tumor imaging using vertical axis-of-rotation (VAOR) SPECT systems: an initial study. *IEEE Trans Nucl Sci.* 44(3):1271-1276.

MP Tornai JE Bowsher, RJ Jaszczak BC Pieper, KL Greer, PM Hardenbergh, RE Coleman. "Effects of Pinhole Material and Aperture Size on Lesion Contrast and Signal-to-Noise in Dedicated Breast SPECT Versus Scintimammography." (Submitted to *J. Nucl. Med.* 2000). Conference presentation at *2000 IEEE Nucl. Sci. Symposium and Med. Imaging Conference*, Lyon, France, Oct. 15-20, 2000, and to be published in *2000 IEEE Conference Record NSS/MIC*.

BC Pieper, JE Bowsher, MP Tornai, KL Greer, J Peter, RJ Jaszczak. "Breast tumor imaging using a tiltable head SPECT camera." Submitted to *2000 IEEE NSS/MIC Conference Record*.

M Ivanovic, DA Weber, S Loncaric. 1997. "Multi-Pinhole Collimator Optimization for High Resolution SPECT Imaging." *Conference Record of the 1996 IEEE Nucl. Sci. Symp. & Med. Imag. Conf.* 1097.

DE Wessell, BMW Tsui, EC Frey, SS Karimi. 1998. "Rotating Slant-Hole SPECT Scintimammography: An initial Investigation." *Conference Record of the 1997 IEEE Nucl. Sci. Symp. & Med. Imag. Conf.* 1145-9.

WW Moses, SE Derenzo, GJ Gruber, RH Huesman, TE Budinger. 1997."Potential for SPECT Cameras Utilizing Photodiode Readout of Scintillator Arrays." *J. Nucl. Med.* 38(5):31P. (Abstract).

R Pani, A Soluri, R Scafè, R Pellegrini, G De Vincentis, F Scopinaro, MN Cinti, L lndovina, G Trotta, M Gambaccini, A Fantini, A Taibi, A Olivo, S Pani, L Rigon, D Bollini, N Lanconelli, E Cisbani, A Del Guerra. "Feasibility Study for SPECT Mammography Based on Compact Imagers Rotating around Breast Vertical Axis." Conference presentation at *2000 IEEE Nucl. Sci. Symposium and Med. Imaging Conference*, Lyon, France, Oct. 15-20, 2000, and to be published in *2000 IEEE Conference Record NSS/MIC*.

MP Tornai, JE Bowsher, CN Archer, J Peter, LR MacDonald, BE Patt, JS lwanczyk, RJ Jaszczak, RE Coleman. "Dedicated Breast Imaging with an ASET: Application Specific Emission Tomograph." Presented at the *48th Society of Nuclear Medicine Meeting*, Toronto, Canada Jun. 23-27, 2001. (Abstract).

S Majewski, E Curran, C Keppel, D Kieper, B Kross, A Palumbo, V Popov, AG Weisenberger, B Welch, R Wojcik, MB Williams, AR Goode, M More, G Zhang. "Optimization of Dedicated Scintimammography Procedures Using Small Prototypes and Compressible Phantoms." Conference presentation at *2000 IEEE Nucl. Sci. Symposium and Med. Imaging Conference*, Lyon, France, Oct. 15-20, 2000, and to be published in *2000 IEEE Conference Record NSS/MIC*.

M Singh, E Mumcuoglu. 1998. "Design of a CZT Based BreastSPECT System." *IEEE Trans. Nucl. Sci. Symp.*NS-45(3):1158-1165.

S Genna, AP Smith. 1988. "The Development of ASPECT, an Annular Single Crystal Brain Camera for High Efficiency SPECT." *IEEE Trans Nucl Sci.* 35(1):654-658.

S Genna, V Gayshan, AP Smith. 1997. "Scintillation Camera for proximate SPECT imaging of an Isolated Breast." *J Nucl Med.* 38(5):32P.

CHJ Chang, JL Sibala, SL Fritz, et al. 1978. "Computed Tomographic Evaluation of Breast." *Am J Roentgenol.* 131(3):459-464.

CHJ Chang, JL Sibala, SL Fritz, et al. 1979. "Specific Value of Computed Tomographic Breast Scanner (CT-M) in diagnosis of Breast Diseases." *Radiology.* 132(3):647-652.

JJ Gisvold, DF Reese, PR Karsell. 1979. "Computed Tomographic Mammography (CTM)." *Am J Roentgenol.* 133(6):1143-1149.

CHJ Chang, JL Sibala, SL Fritz, et al. 1980. "Computed-Tomography in Detection and Diagnosis of Breast Cancer." *Cancer.* 46(4):939-946.

JWT Muller, PFGM Van Waes, PR Koehler. 1983. "Computed-Tomography of Breast-Lesions—Comparison with X-Ray Mammography." *J Comput Assist Tomo.* 7(4):650-654.

K Iwata, MC Wu, B Hasegawa. "Design of combined X-ray CT and SPECT systems for small animals." *1999 IEEE Nuclear Science Symposium. Conference Record.* 3:1608-12.

T Beyer, DW Townsend, T Brun, PE Kinahan, M Charron, R Roddy, J Jerin, J Young, L Byars, and R Nutt. 2000. "A combined PET/CT scanner for clinical oncology." *J Nucl. Med.* 2000 41: 1369-1379.

WR Jewel, JH Thomas, CHJ Chang, 1983. "Computed Tomographic Mammography Directed Biopsy of the Breast." *Surg Gynecol Obstet.* 157(1):75-76.

RR Raylman, S Majewski, R Wojcik, AG Weisenberger, B Kross, V Popov, JS Schreiman, Ha Bishop. "An apparatus for positron emission mammography guided biopsy." *1999 IEEE Nuclear Science Symposium Conference Record.* 3:1323-7.

SD Metzler, JE Bowsher, MP Tornai, BC Pieper, J Peter, RJ Jaszczak. SPECT breast imaging combining horizontal and vertical axes of rotation Conference presentation at *2000 IEEE Nucl. Sci. Symposium and Med. Imaging Conference, Lyon, France, 15-20 Oct. 2000, and to be published in 2000 IEEE Conference Record NSS/MIC.* Submitted to *IEEE Trans Nucl Sci.*

RJ Jaszczak, DR Gilland, JW McCormick, C Scarfone, RE Coleman. 1996. The Effect of Truncation Reduction in Fan Beam Transmission for Attenuation Correction of Cardiac SPECT. *IEEE Trans. Nucl. Sci.* NS43(4):2255-2262.

RJ Jaszczak, DR Gilland, MW Hanson, S Jang, KL Greer, RE Coleman. 1993. Fast transmission CT for determining attenuation maps using a collimated line source, rotatable air-copper-lead attenuators, and fan beam collimation. *J. Nucl. Med.* 34:1577-1586.

W Chang, S Loncaric, G Huang, P Sanpitak. 1995. Asymmetric fan transmission CT on SPECT systems. *Phys. Med. Biol.* 40:913-928 (Abstract).

MA King, DS Luo, ST Dahlberg, BC Penney and HT Morgan; 1994; Transmission and emission SPECT imaging of attenuator and source distributions larger than the camera field of view; J. Nuclear Medicine; (No. 364) 92P (Abstract).

EG Hawmann, EP Ficaro, JJ Hamill and M. Schaiger; 1994. Fan beam collimation with off center focus for simultaneous emission/transmission SPECT in multi-camera SPECT systems. J. Nuclear Medicine.(No. 365) 92P (Abstract).

DR Gilland, RJ Jaszczak, TG Turkington, RE Coleman. 1998. Comparison of transmission acquisition approaches for SPECT nonuniform attenuation compensation. *IEEE Trans. Nucl. Sci.* NS45(3):1244-1249.

MP Tornai, RJ Jaszczak, DR Gilland, RE Coleman, Y Ooie, M Taguchi, G Enos. 2000. "Investigation of Large Field-of-View Transmission Imaging for SPECT Attenuation Compensation with Gd-153, Tc-99m and Ce-139 Sources." *IEEE Trans. Nucl. Sci.* NS-47(3):1182-1191.

MA King, BMW Tsui, T-S Pan. 1995. Attenuation compensation for cardiac single-photon emission computed tomographic imaging: Part 1. Impact of attenuation and methods of estimating attenuation maps. *J. Nucl. Cardiol.* 2:513-524.

GT Gullberg. 1998. Innovative design concepts for transmission CT in attenuation corrected SPECT imaging. [Editorial] *J. Nucl. Med.* 39(8):1344-1347.

MA King, D Luo, ST Dahlberg, BJ Villegas, BC Penney, HT Morgan. 1996. Transmission imaging of large attenuators using a slant hole collimator on a three-headed SPECT system. *Med. Phys.* 23:263-272.

EP Ficaro, JA Fessler, WL Rogers, M Schwaiger. 1994. Comparison of americium-241 and technetium-99m as transmission sources for attenuation correction of thallium-201 SPECT imaging of the heart. *J. Nucl. Med.* 35:652-663.

GT Gullberg, HT Morgan, GL Zeng, PE Christian, EVR DiBella, CH Tung, PJ Maniawski, YL Hsieh, FL Datz. 1998. The Design and performance of a Simultaneous Transmission and Emission Tomography System. *IEEE Trans. Nucl. Sci.* NS45:1676-1698.

B Chen, R Ning. "Cone-beam volume CT mammographic imaging: feasibility study." Recent conference presentation at *2001 SPIE Med. Imaging Conference*, San Diego, CA, Feb. 17-23, 2001.

MP Tornai, Bowsher, Archer, Peter et al; "A New Approach to Application Specific Emission Tomography of (ASET) of the Breast"; 1st Topical Symposium on Functional Breast Inaging with Advanced Detectors 18-20, Apr. 2001, Rome Italy.

Nuclear Science Symposium and Medical Imaging Conference; 3.10—MIC Instrumentation Systems and Medical Imaging—SPECT, Imaging Geometry and Collimators; Lyon France Oct. 15-20, 2000.

MP Tornai, Bowsher, Archer, Peter et al; Dedicated Breast Imaging with an ASET: Application Specific Emission Tomograph; The Society of Nuclear Medicine Meeting; Toronto, Canada Jun. 23-27, 2001.

Pieper et al; "Breast Tumor Imaging Using a Tiltable Head SPECT Camera"; IEEE Transactions on Muclear Science, No. 2000.

Brochure; "High-Performance Annular Rotation Stages"; RV Series; Newport; pp. 3-6-3-11; No Date.

Brochure; "Opto-Mechanical Drawings"; Newport; p. 22-94-22-95; No Date.

Brochure; "Goniometric Cradles"; BGM Series; Newport pp. 3-24-3-29; No Date.

Tornai; "A Novel SPECT System for Breast Imaging"; Biomedical Engineering Research Grants; Investigator Abstracts; Apr. 2000; pp. 1-33; See pp. 27 and 28.

Drouilhet; "Duke Professor Receives Grant for Imaging System"; The Lion's Roar Online; vol. 72, Issue 9; 2 pages; Oct. 5, 2000.

Djuranovic "Researcher Examines New Breast Cancer Detection System"; The Chronicle Online, vol. 96; Issue 29, Oct. 4, 2000; 4 pages.

"Duke Radiologist To Study Breast Imaging"; Duke University Medical Center; Sep. 26, 2000; http://www.dukenews.duke.edu/Med/whitaker.htm.

CHJ Chang, DE Nesbit, DR Fischer, et al. 1982. "Computed Tomographic Mammography Using a Conventional Body Scanner." *Am J Roentgenol.* 138(5):553-558.

Doshi; Silverman, Shao and Cherry; "maxPET: A dedicated mammary and axillary region PET imaging system for breast cancer"; IEEE Trans Nucl Sci. vol. 48, No. 3, Jun. 2001; pp. 811-815.

M. Tornai et al; "A novel application specific emission tomograph (ASET) for breast imaging"; IEEE 2001 Conference; 5 pages.

Archer et al; "Implementation and initial characterization of acquisition orbits about a pendulous breast using the ASET system"; IEEE 2001 Conference; 4 pages.

Tang et al; "Implementation of a combined X-ray CT scintillation camera imaging system for localizing and measuring radionuclide update; experiments in phantoms and patients"; IEEE Trans. Nucl. Sci; vol. 46, No. 3; Jun. 1999; pp. 551-557.

Hasegawa et al; "Implementation and applications of a combined CT/SPECT system"; IEEE 1999 Conference; 5 pages.

JA Patton; D. Delbeke and M. Sandler; "Image fusion using an integrated, dual-head coincidence camera with X-ray rube-based attenuation maps"; J. of Nucl. Med. ; vol. 41, No. 8; Aug. 2000; pp. 1364-1368.

W Chang; S. Loncaric, G. Huang and P. Sanpitak; "Asymmetric fan transmission CT on SPECT systems"; Phys. Med. Biol. 40 (1995) 913-928.

Ning et al; "Flat panel detctor-based cone beam volume CT breast imaging: preliminary phantom study";Conference Feb. 17-22, 2001; 10 pages.

Archer et al, "Implementation and Initial Characterization of Acquisition Orbits About a Pendulous Breast Using the ASET System", pp. 1323-1327, IEEE 2002.

Archer et al, "Implementation and Initial Characterization of Acquisition Orbits With a Dedicated Emission Mammotomograph", pp. 413-420, IEEE Transactions on Nuclear Science, vol. 50, No. 3, Jun. 2003.

Brzymialkiewicz et al, "Evaluation of Fully 3-D Emission Mammotomography With a Compact Cadmium Zinc Telluride Detector", pp. 868-877, IEEE Transactions on Medical Imaging, vol. 24, No. 7, Jul. 2005.

Madhav, et al "Evaluation of tilted cone-beam CT orbits in the development of a dedicated hybrid mammotomograph", pp. 1-17 (not yet published).

* cited by examiner

APPLICATION SPECIFIC EMISSION AND TRANSMISSION TOMOGRAPHY

CROSS-REFERENCES TO RELATED APPLICATIONS

This application claims the benefit of U.S. Provisional Application Ser. No. 60/279,660, which was filed Mar. 30, 2001, the entire disclosure of which is incorporated herein by this reference. This application also claims the benefit of U.S. Provisional Application Ser. No. 60/283,383, which was filed Apr. 13, 2001, the entire disclosure of which is incorporated herein by this reference.

STATEMENT REGARDING FEDERALLY SPONSORED RESEARCH OR DEVELOPMENT

This invention was made with Government support under NIH/NCI grants RO1-CA76006 and RO1-CA33541, and DOE grant DE-FG02-96ER62150. The Government may have certain rights in this invention.

BACKGROUND AND SUMMARY OF THE INVENTION

There is broad interest in the application of Nuclear Medicine (NM) techniques with compounds of various specificity to functional imaging of breast lesions. The use of these compounds can be for confirmation of metastases based on the functional information, facilitating identification of cancerous lesions in women with large or especially dense breasts which particularly cause diagnostic problems in x-ray mammographic screening, and also as a way to monitor any treatment or therapy the patient receives. The efficacy of single photon emitting tracers versus positron emitting tracers remains debatable, yet the high sensitivities and specificities (~90%) already achieved with breast imaging for $\geq 1$ cm diameter lesions, as well as commercial availability of agents specifically targeted for breast tumor imaging, lend credence to the efficacy of the use of these various compounds. For example, in studies of women with suspicious mammograms, 2-dimensional planar imaging of $\geq 1$ cm diameter breast tumors using single photon emitting $^{99m}$Tc-labeled sestamibi or $^{99m}$Tc-methylene-diphosphonate achieved sensitivities and specificities of ~90%. While these results are encouraging in the specific population sample, dedicated 3-dimensional NM tomographic imaging with single photon emission computed tomography (SPECT) or positron emission tomography (PET), with superior lesion contrast and signal-to-noise ratio (SNR) characteristics could further improve diagnoses for this group, and potentially be applied more generally.

Conventional whole body SPECT imaging for breast disease is primarily limited by the resolution degradation resulting from the necessarily large radius of rotation (ROR) required to rotate the large and bulky camera system about the patient. Furthermore, additional problems include torso attenuation, primary and scatter contamination from cardiac or hepatic uptake of the tracer, as well as increased breast lesion scatter itself with supine dependant imaging of the breast. Tomographic, whole body SPECT imaging (3-dimensional, multiple projection angles) for breast imaging compared with planar scintimammography has yielded poorer imaging, and hence poorer diagnostic results than expected despite the improved lesion contrast and SNRs otherwise expected with SPECT. Thus, there is currently a strong notion that there is little added utility in conventional SPECT imaging for breast disease, despite the fact that there should, in principle, be much higher contrast of deeply seated lesions, especially with correctly applied, dedicated tomographic imaging techniques. Thus, the main reasons for these shortfalls are that (1) whole body SPECT requires large ROR, which substantially degrades spatial resolution for (small, <1 cm diameter) lesion visualization; (2) for posterior camera locations, the body attenuates the signal coming directly from the breast; and (3) there is substantial contamination of the lesion signals from cardiac and hepatic signals (primary and scattered radiation) where the $^{99m}$Tc-labeled radiopharmaceutical compounds are also taken up, resulting in artifacts throughout the breast in reconstructed images.

Due to the increasing intensity in radiochemistry with PET radiopharmaceuticals and their growing availability from localized distribution centers throughout the United States, there is also great interest in the detection of coincident photons with whole body PET scanners. However, the clinical results with whole body PET are similar to those with whole body SPECT in that the effects of photon attenuation and scatter from the torso cause image artifacts and hence the potential for missed small breast lesions.

In contrast to current clinical whole body imaging protocols for evaluating breast disease, there are various dedicated NM breast imaging approaches currently under investigation with PET and SPECT. The simplest approach utilizes planar, single photon imaging (2-dimensional, single projection angle) with clinical gamma cameras ($\geq 800$ cm$^2$ detector surface area) using various types of collimators. This basic approach, with very fine resolution parallel hole single photon collimators yielded the ~90% sensitivity and specificity results for NM breast lesion detection and visualization described above.

Some dedicated breast SPECT approaches utilizing clinical gamma cameras with prone dependant breast have demonstrated that application specific tomographic imaging of the breast compared with planar imaging may provide improved images of breast lesions. See, e.g., Li et al., Limited angular view MLEM pinhole SPECT for breast tumor detection. J Nucl Med. 37(5):214P; Scarfone et al., Breast tumor imaging using incomplete orbit pinhole SPECT: a phantom study. Nuc Med Commun. 18:1077-1086; Wang et al., Prone breast tumor imaging using vertical axis-of-rotation (VAOR) SPECT systems: an initial study. IEEE Trans Nucl Sci. 44(3): 1271-1276; and La Riviere et al., Ideal-observer analysis of lesion detectability in planar, conventional SPECT, and dedicated SPECT scintimammography using effective multi-dimensional smoothing. IEEE Trans Nuc Sci, 45(3):1273-1279, 1998. The various dedicated breast SPECT studies that employed clinical gamma cameras were, however, still limited by the large detector sizes that cannot achieve close proximity to the breast volume of interest. Since spatial resolution rapidly falls off with increasing distance in single photon imaging, these systems are limited in the object sizes that they can resolve. Even those systems that employ pinhole collimators, which generally have better sensitivity and resolution than parallel hole collimators at small separations or ROR, are limited in resolution since the breast volumes are not necessarily "small", and there is severe axial blurring and other sampling artifacts which may limit the usefulness of the data to relatively small breast volumes.

Dedicated, small area gamma cameras ($\leq 400$ cm$^2$ in area) have further demonstrated improved visualization of small tumor phantoms in compressed breast, planar geometries but are limited by low image contrast resulting from planar imaging, and, additionally, cannot provide 3-dimensional localization within the breast volume.

Some dedicated coincidence devices have been proposed for Positron Emission Mammography (PEM, which is a limited angle, non-fully tomographic cousin of PET) and successfully implemented on clinical x-ray mammographic devices so that there is inherent coregistration between x-ray mammograms and the functional PEM data. Furthermore, while full PET ring devices have been proposed, the dedicated devices have to date all been implemented in a static, approximately coplanar mode with opposed detector plates of various geometry. These approaches have limited quantitative and depth information in the volume of the (un)compressed breast geometries investigated and are akin to the single photon planar imaging approaches. It is unclear if these devices will prove clinically efficacious due to their inherent limitations.

In view of the shortfalls of the above noted imaging techniques, an object of the invention was to design a tomographic gantry for imaging metabolically active lesions in the pendant breast. This system overcomes physical constraints associated with imaging a pendulous breast in prone patients, while simultaneously satisfying sampling criteria for sufficient data collection in the pendulous breast reference frame. Thus, in one embodiment, the invention provides a compact and mobile gantry for 3-dimensional Application Specific Emission and/or Transmission Tomography (ASETT) imaging of the breast in single photon or coincidence emission modes, and single photon, coincident photon, or x-ray transmission modes.

More generally, the invention is embodied in an imaging system for generating images of a body part suspended within an imaging area of the system, comprising a support having a rotation axis extending through the imaging area and at least one imaging device having an imaging device axis which passes through a first imaging device field of view, the imaging device being mounted to the support so as to be selectively movable in three dimensions, including radial movement relative to the rotation axis, rotational movement about the rotation axis, vertical movement parallel to the rotation axis, and pivoting movement about a pivot axis perpendicular to the rotation axis, whereby the imaging device can be selectively moved along a path that defines a curved 3-dimensional surface. In an exemplary embodiment, the imaging device axis is laterally offset from the rotation axis and the support is mounted for rotational movement through at least about 180 degrees, whereby when the body part is greater than the imaging device field of view, an entire volume of the body part can be sufficiently sampled to accurately reconstruct the emission activity distribution.

The results of preliminary work with the system of the invention demonstrate the feasibility of a single compact emission imaging camera mounted on a versatile gantry to image the breast and associated axillary region. This work can be extended to include coincident detector systems placed on the gantry of the invention and used to acquire PET images of the breast. Furthermore, an x-ray transmission imaging system for dedicated breast computed tomography (CT) is also viable for use with this ASETT system, and its novel features are described.

Furthermore, fully tomographic transmission data (3-dimensional) which differs from partial view planar scans (2-dimensional) can also be used in both SPECT and PET for attenuation correction of the emission data. This highly accurate structural transmission map ultimately leads to more quantitatively accurate functional data from which parameters like metabolic rates of reaction can be determined to monitor therapeutic progress and determine tissue necrosis versus tumor recurrence in a patient. Simply having a structural framework (the structural x-ray CT image) with which to identify the location of the focal radioactive uptake with NM imaging (often a diffuse or ambiguously localized region of greater signal) may be enough to aid in breast lesion image assessment alone.

Due to some physical constraints associated with imaging a single pendant breast with maximal separation from the nearby body containing background, SPECT techniques which employ cameras whose line-of-sight of the activity distributions are determined by collimators of various solid geometries (e.g. parallel beam, fan beam, cone beam, pinhole, slanted, angled, etc.) may have some physical advantages compared with PET techniques. Moreover, placing dedicated SPECT cameras in close proximity to the breast (or other object of interest, e.g. the prostate) to fully sample the object volume is critical to obtaining complete data for quantitatively imaging small lesions and/or lesions with low radiopharmaceutical uptake, which is ultimately a determining factor in fully exploiting the power of functional imaging and volumetric localization in the breast or other organs.

There are various anticipated advancements gained with a high performance, dedicated tomographic system embodying the invention including improved SNR and contrast characteristics due to (1) the improved intrinsic spatial and energy resolution potentially afforded by dedicated, compact, high performance imaging systems which can therefore minimize scatter contamination, (2) the closer achievable proximity to the object of interest with more compact imaging systems which improves collimator-limited spatial resolution for SPECT, and (3) due to (2) the camera will preferentially view the breast and minimally view signals from other regions of the body. These advancements should result in an ability to image and 3-dimensionally localize smaller (<1 cm diameter), non-palpable and potentially pre-metastatic tumors in a larger population with smaller variance and bias. The use of multiple ASETT scans over time with NM techniques can guide treatments, monitor therapy, and help evaluate outcomes. The use of combined structural and functional imaging may help even further in patient management and care.

Both the structural and functional volumetric information could potentially be used to guide needle biopsies more accurately than with current planar approaches which have limited depth information; more accurate needle guidance could improve the needle localization, hence lower false positives, and overall improve diagnosis and guide decisions about treatment protocols for patients.

BRIEF DESCRIPTION OF THE DRAWINGS

These, as well as other objects and advantages of this invention, will be more completely understood and appreciated by careful study of the following more detailed description of the presently preferred exemplary embodiments of the invention taken in conjunction with the accompanying drawings, in which.

DETAILED DESCRIPTION OF INVENTION

In view of the shortfalls of whole body and/or 2-dimensional imaging techniques for imaging breasts, in particular, a tomographic gantry was designed, built and evaluated for imaging metabolically active lesions in the pendant breast of a prone patient. This system overcomes physical constraints associated with imaging a pendulous breast, while simultaneously satisfying sampling criteria for sufficient data collection in the pendulous breast reference frame.

More specifically, the invention provides a compact and mobile gantry for 3-dimensional Application Specific Emission and/or Transmission Tomography (ASETT) imaging of the breast in single photon or coincidence emission modes, and single photon, coincident photon, or x-ray transmission modes. The open gantry geometry also facilitates the incorporation of transmission x-ray computed tomography (CT) simultaneously with the emission detector system(s) from which valuable structural and attenuation information about the imaged object of interest can be gained. Furthermore, by incorporating these systems on a single gantry, the resulting reconstructed structural transmission and functional emission images can be registered since there is already an inherent co-registration in these simultaneously acquired data.

Figure 1:
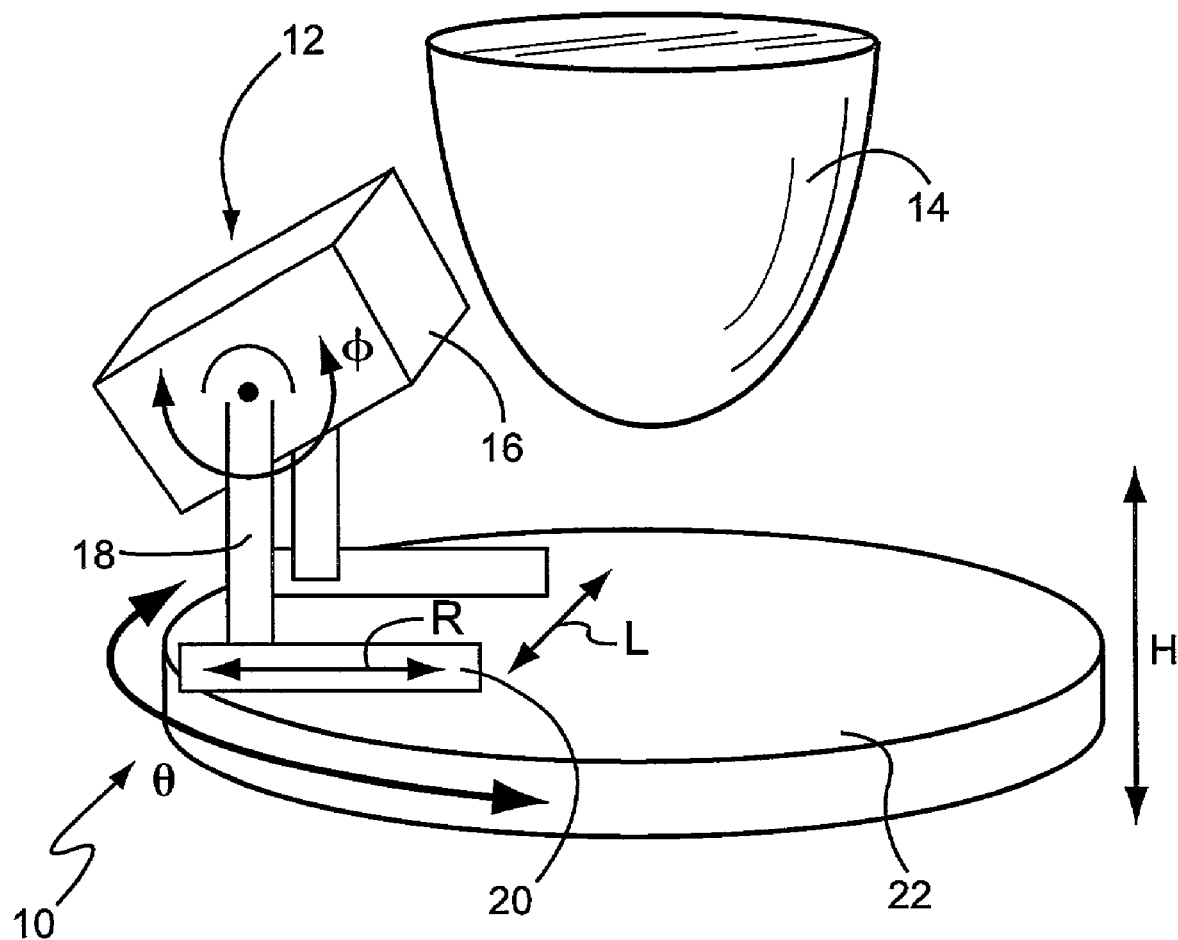
FIG. 1 is a schematic perspective view of an imaging device gantry system embodying the invention for achieving 3-dimensional close proximity to a breast or other volume of interest.
Figure 2:
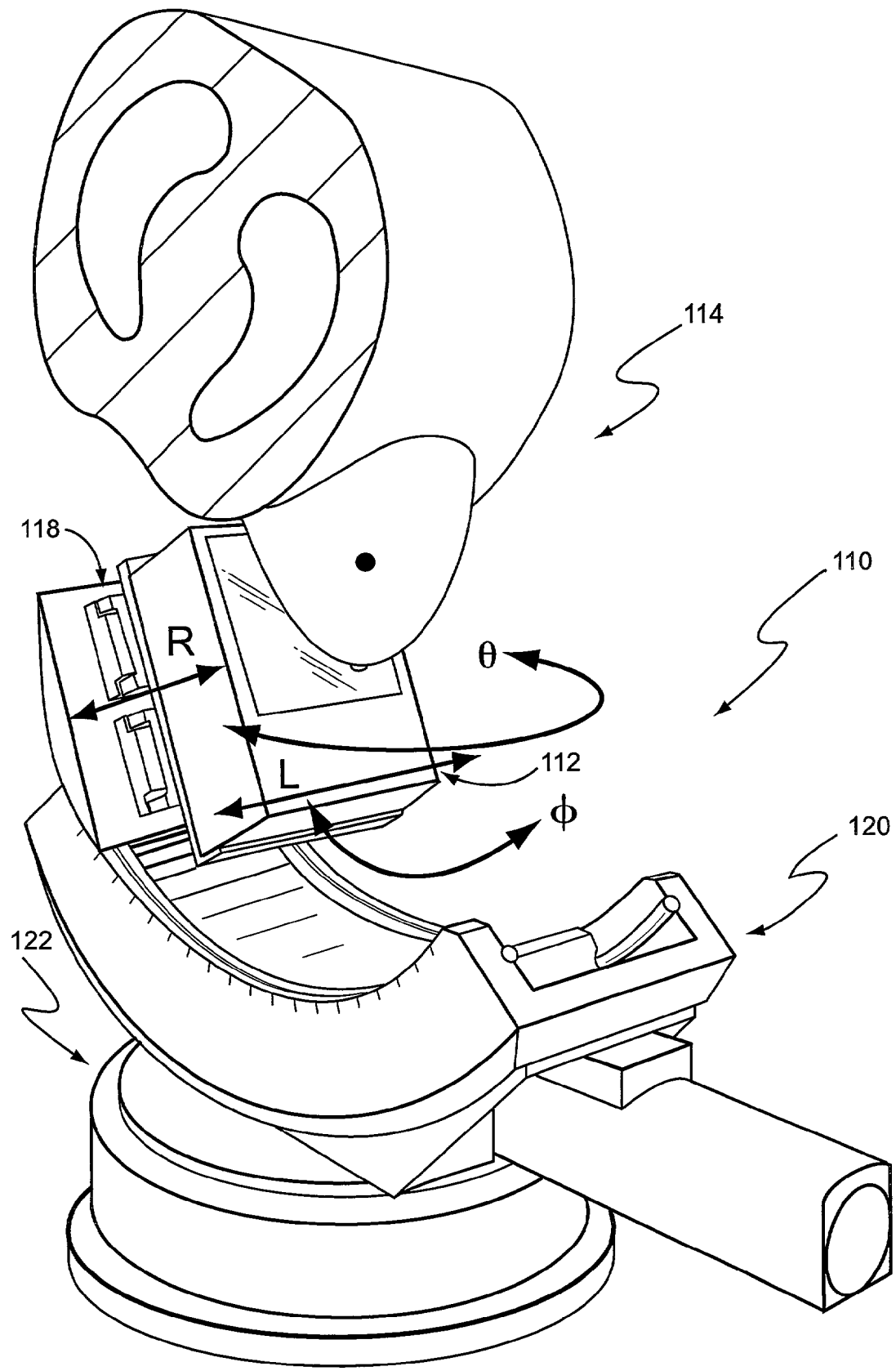
FIG. 2 is a perspective view of a prone torso segment and breast with the breast center-of-mass located approximately in the center of the field of view and center-of-rotation of an application specific emission tomography camera system according to a first exemplary embodiment of the invention, concentric with the breast rotation axis, with the camera at a polar angle ($\phi$) of about 30°.
Figure 3:
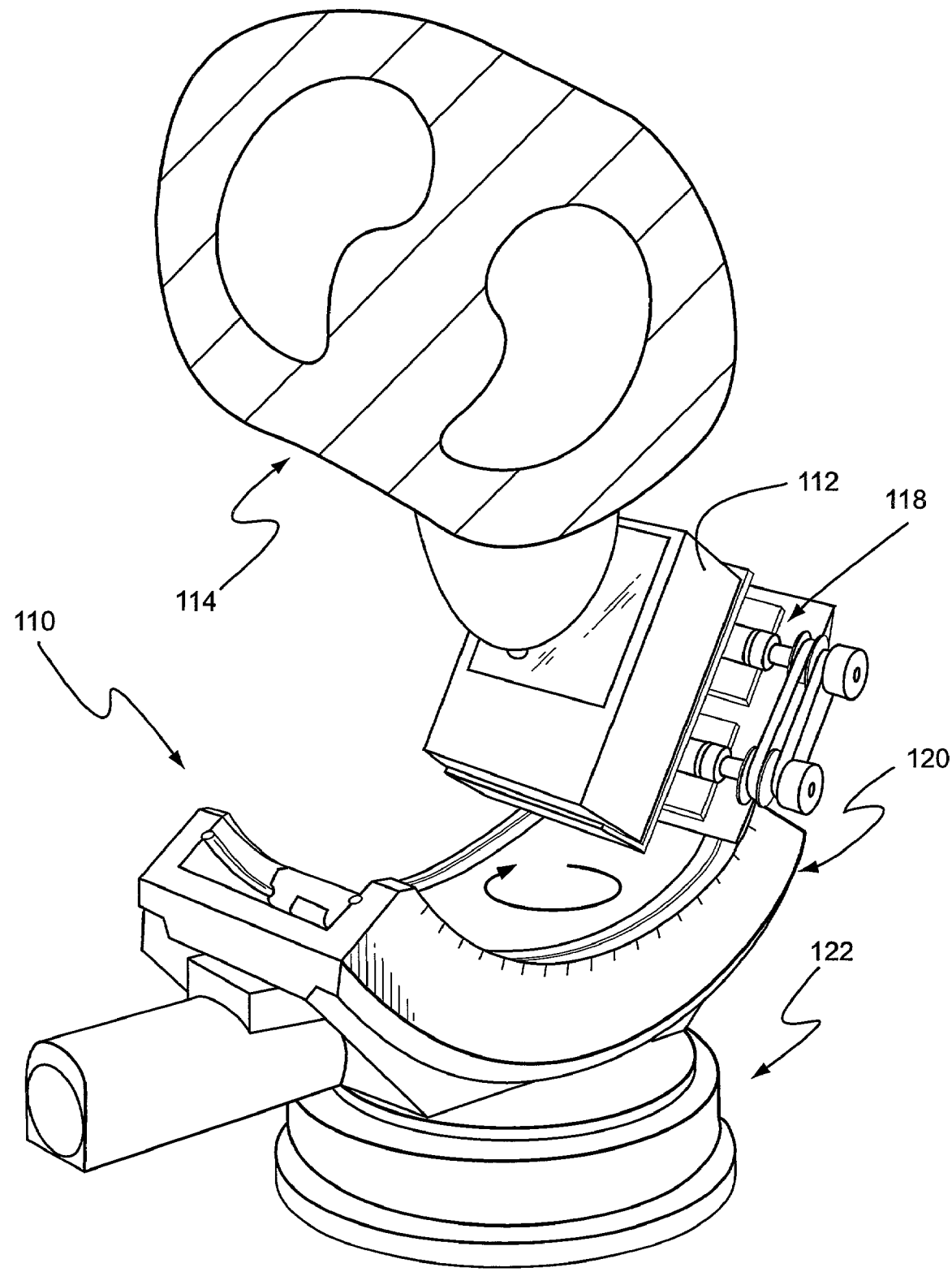
FIG. 3 is a perspective view of the imaging device gantry system of FIG. 2 after having rotated in the direction of angle θ through an angle of about 135°.
Figure 4:
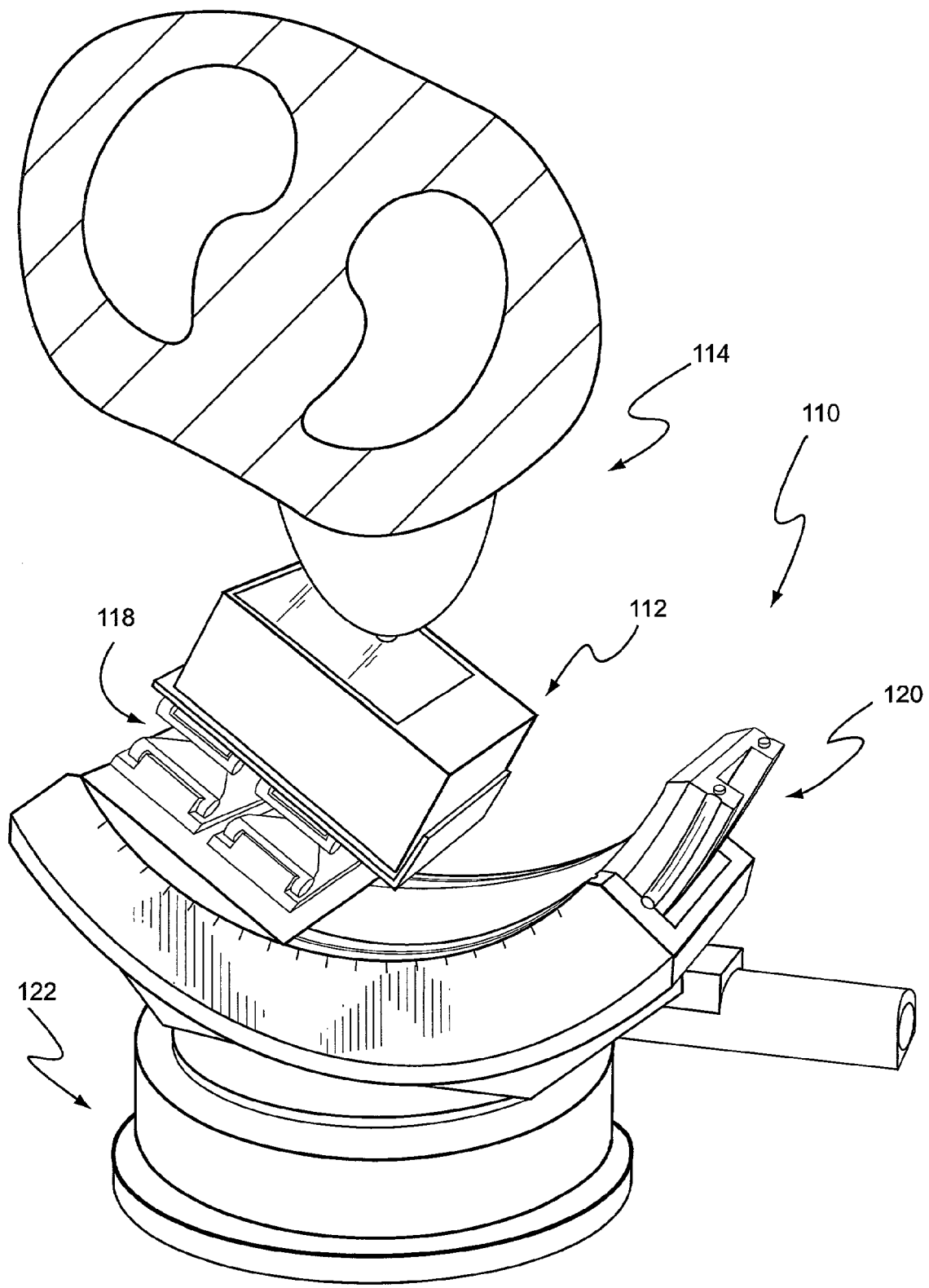
FIG. 4 is a perspective view of the imaging device gantry system of FIG. 2 with the imaging device disposed at a polar angle (φ) of about 60°.
Figure 5:
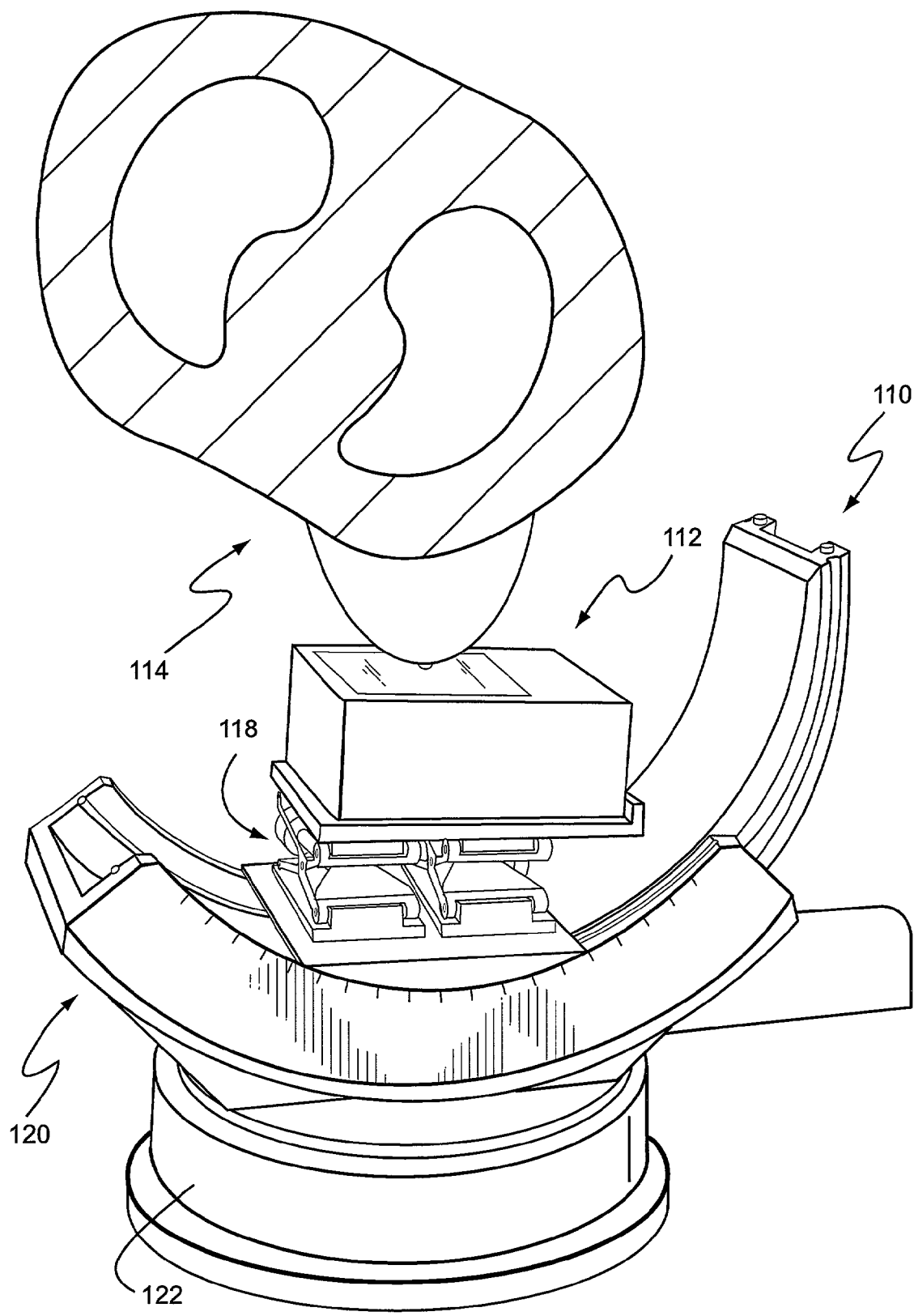
FIG. 5 is a perspective view of the imaging device gantry system of FIG. 2 with the imaging device at a polar angle (φ) of about 90°.
Figure 6:
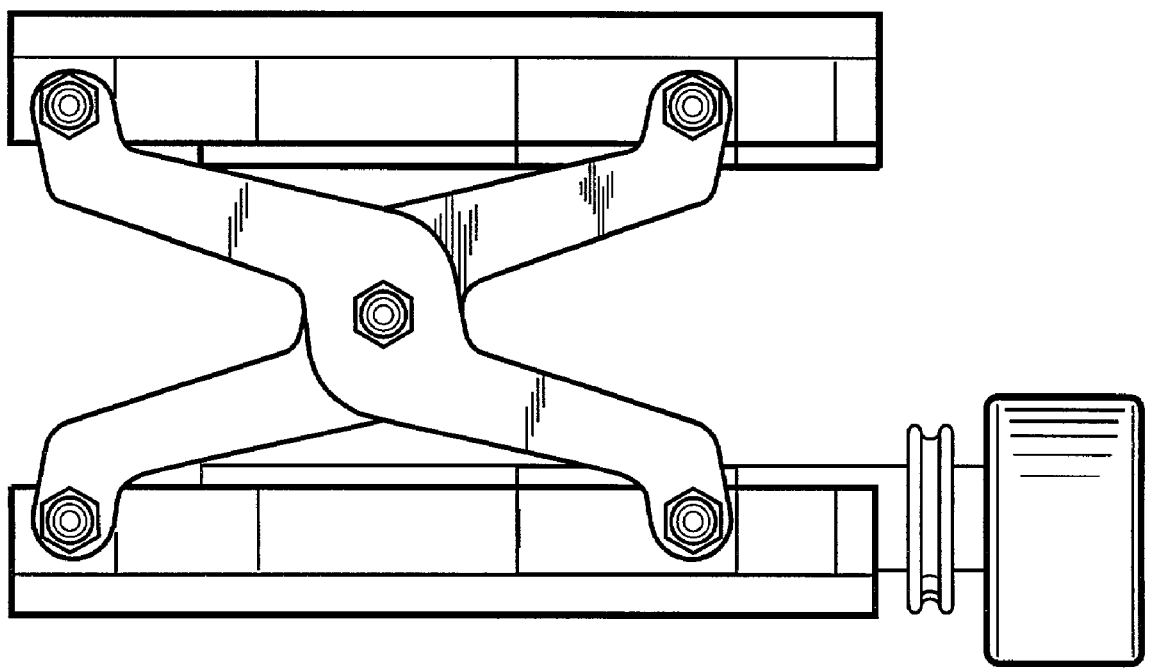
FIG. 6 is an elevational view of an imaging device support for adjusting the radial position (R) of the imaging device.
Figure 7A:
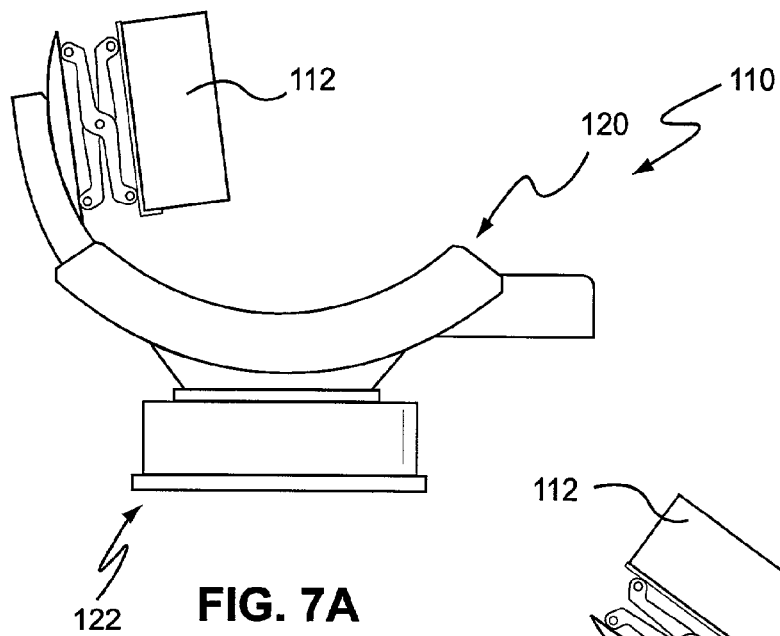
FIG. 7A is a schematic elevational view of an imaging device gantry system embodying the invention with a single imaging device disposed at a polar angle (φ) of about 0°.
Figure 7B:
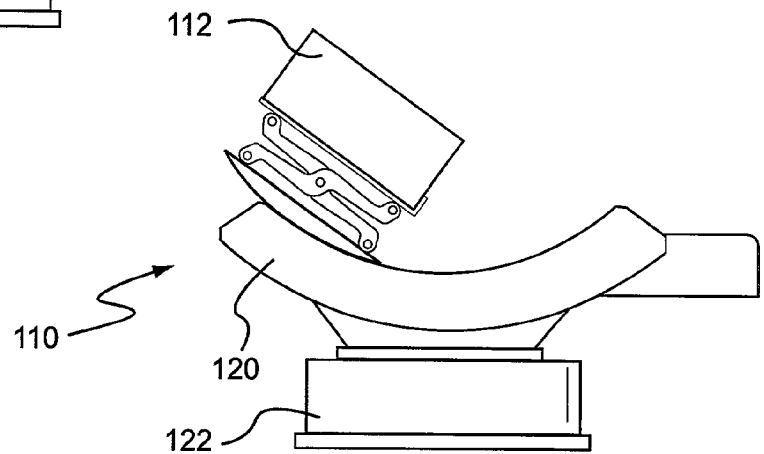
FIG. 7B is a schematic elevational view of an imaging device gantry system embodying the invention with the imaging device disposed at a polar angle (φ) of about 45°.
Figure 7C:
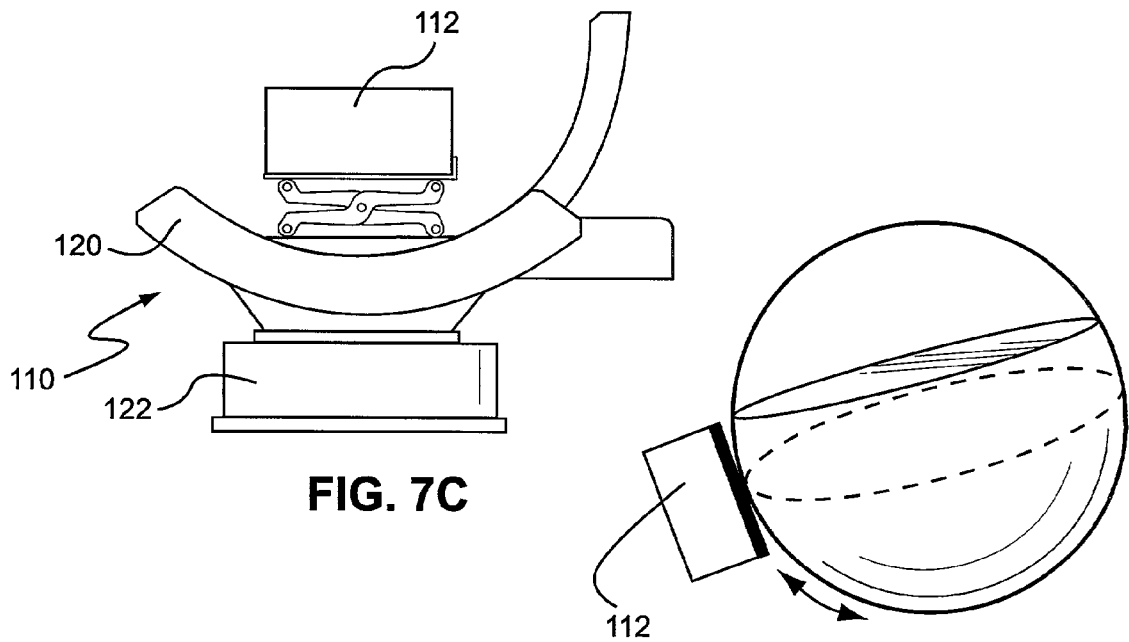
FIG. 7C is a schematic elevational view of an imaging device gantry system embodying the invention with the imaging device disposed at a polar angle (φ) of about 90°.
Figure 7D:
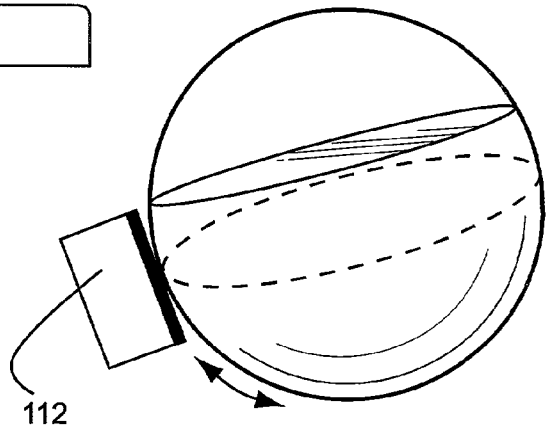
FIG. 7D is a schematic illustration of the region that can be imaged with the imaging device and gantry system illustrated in FIGS. 7A-C, with a single camera mounted near an end of the cradle.

Thus, a key aspect of this invention was the development of a dedicated, highly accurate and versatile two stage gantry. More specifically, to provide for dedicated 3-dimensional NM tomographic imaging with single photon emission computed tomography (SPECT) an imaging device gantry system had to be developed that could achieve angular, lateral and height or radial adjustments that support the imaging device in close proximity to the target breast. Such a gantry 10 is schematically illustrated in FIG. 1. The imaging device, schematically shown at 12, is supported by the gantry 10 so that it can be disposed generally parallel to and closely adjacent the target breast 14. Thus, the imaging device support is mounted so that the emission receiving face 16 of the imaging device 12 can be selectively disposed parallel to and adjacent the surface of the breast 14. As shown in FIG. 1, this may be accomplished by pivotally mounting (as shown by arrow φ) the imaging device 12 to a support assembly 18 that can itself be radially displaced in direction R, e.g., along a track 20 or other translation assembly. This system can be further laterally displaced along a similar track (not shown) or other translation assembly, as schematically shown by arrow L. To allow the imaging device to track the periphery of the breast, closely adjacent the breast, the track assembly 20 is mounted for rotation as shown by angle theta (θ) and at least one of the imaging device support assembly 18. The track assembly 20, and/or the rotary mount 22 is height adjustable as shown generally by arrow H.

An exemplary embodiment of an Application Specific Emission and/or Transmission Tomography (ASETT) gantry system, with only an emission system mounted to it will now be described with reference to FIGS. 2-7. In preliminary studies, an anthropomorphic phantom 114 filled with various concentrations of $^{99m}$Tc pertechnetate (140.6 keV) activity and water, and suspended in a prone position was used to simulate the prone patient, as schematically illustrated in FIGS. 2-5.

In principle, any compact gamma camera could be employed on the dedicated ASETT gantry 110 as the imaging device 112 and used with a generalized SPECT reconstruction algorithm. For the initial studies the currently available, FDA 510k approved, compact LumaGEM™ gamma camera and data acquisition system (Gamma Medica, Inc., Northridge, Calif.) was used. This camera utilizes 2×2×6 mm$^3$ optically isolated, quantized NaI(T1) scintillators on 2.2 mm center-to-center spacing arranged in a 58×58 element 2-dimensional array; these scintillators are optically coupled to compact position sensitive photomultiplier tubes (Hammamatsu Ltd., Tokyo, Japan) with custom high-voltage and readout electronics. The camera's useful field-of-view (FOV) is <13×13 cm$^2$ and is equal to the entire FOV. There are continual development efforts by several groups to develop ultra-compact, scintillator-photomultiplier as well as non-photomultiplier, solid-state, high-atomic number, compound semiconductor based detectors with very high performance characteristics. Other imaging devices, including such detectors may be provided as imaging device 12/112, without departing from the invention hereof.

The imaging device 112, e.g. the compact gamma camera in an exemplary embodiment, is mounted to a gantry system 110 that can achieve angular, radial, and height adjustments, and potentially lateral adjustments, and supports and disposes the imaging device in close proximity to, e.g., the target breast. In an exemplary embodiment, then, in addition to the necessary camera(s) 112, the gantry includes a large goniometric stage and cradle 120 that allows nominally ±45° angular motion on a radius of rotation (ROR) of about 246 mm. In the illustrated embodiment, the camera is located at a 45° angle relative to the centerline of the goniometer 120. The goniometric stage and cradle used in the preliminary studies was model BGM200, Newport Corp, Irvine, Calif. A larger cradle or one that allows greater than ±45° angular motion could also be used to extend the positioning range of the camera, e.g. up to ±180° to provide a full circle view. In addition or in the alternative, the entire system may be angled, e.g. disposed on a wedge of adjustable angles (FIG. 8A-8C), or disposed upside down with respect to the orientation shown with these adjustments and configurations taking into consideration the physical limits imposed by the particular location of the breast or other target portion of the body and the manner in which the patient is supported. As is apparent, the illustrated embodiment of the goniometric cradle 120 allows the camera to trace an arc of about 90° generally following the surface of the pendant breast.

In the illustrated embodiment, radial position, and thus ROR control is provided by mounting the camera or other imaging device on a dual-jack platform 118 (e.g., model M-EL80, Newport Corp, best seen in FIG. 6) that allows approximately 6 cm variations in the camera's ROR with respect to the center-of-rotation (COR) point of the hemispherical geometry. In this embodiment, lateral adjustment as shown by arrow L was provided with plural mounting locations for the camera on the jack platform so that the lateral position of the camera with respect to the gantry and/or the object being imaged could be selectively determined. In the alternative, lateral adjustment may be achieved by providing a linear translator between the jacks and the camera. Furthermore, although not illustrated, the camera can be mounted to swivel or rotate about the camera axis or an axis parallel thereto to provide further adjustment, and thus imaging, options for the operator.

With a motorized dual-jack system, true 3-dimensional ellipsoidal (and other) volumes could be traced out by a fully motorized and computer controlled system. During preliminary studies, sophisticated device control was implemented with a multi-stage (currently two) motor controller (e.g., model ESP7000, Newport Corp.) in order to achieve suitable orbits. As will be understood, mounting the imaging device to a goniometric stage and cradle system provides for concurrent adjustment of tilt ($\phi$), height (H), radius (R), and position (L) as the imaging device is moved about and along the surface of the breast. Initial adjustment of the dual jack platform 118 provides for initial determination of the radius of rotation (ROR) and, as noted above, adjustment during imaging allows the true 3-dimensional shape of the breast to be traced. If desired, the imaging device can be pivotally mounted to the platform of the dual jack for further facilitating the parallel disposition of the imaging device with respect to the surface of the breast.

The entire goniometric stage and cradle system rests on a rotation stage 122 (e.g., model RV350, Newport Corp.), allowing full 360° rotation about the goniometric centerline, referred to herein as the Rotation Axis (RA). Thus, with appropriate ROR control (radial position R), goniometric angular position (polar angle $\phi$), and rotation (azimuthal angle $\theta$) about the RA, the camera can be positioned anywhere in a 2pi solid angle (hemispheres of various radii) about the breast (FIGS. 7A-7D).

Similar to contemporary planar, digital x-ray guided biopsy procedures, a biopsy or tissue extraction device could be mounted on platform 22/122. After image acquisition with either SPECT or PET or x-ray CT, and image reconstruction and interpretation of the data, the 3-dimensional location of some small region of interest can be determined from those images. The precise location of that region within, e.g., the physical breast and gantry framework can be calculated relative to the location of the camera(s) and tissue extraction device, and this information used to guide the tissue extraction device towards that region. In other words, once you have the 3-dimensional image information, and the physician determines that a particular region should be biopsied, the coordinates from the reconstructed image volume can be translated to actual physical coordinates in real space. With these coordinates, the computer can direct the tissue extraction device to that location within, e.g., the breast in real space, and then extract a tissue sample for histology. Since the extraction device and camera location are fixed relative to each other, and there is some general coordinate reference frame (e.g. 'top' is always towards the patient's head and 'bottom' always towards her feet)—also called a stereotactic frame—a needle-like or other (e.g. vacuum, ultrasonic ablator, laser ablator, etc.) extraction device can be guided to the identified region.

Figure 8A:
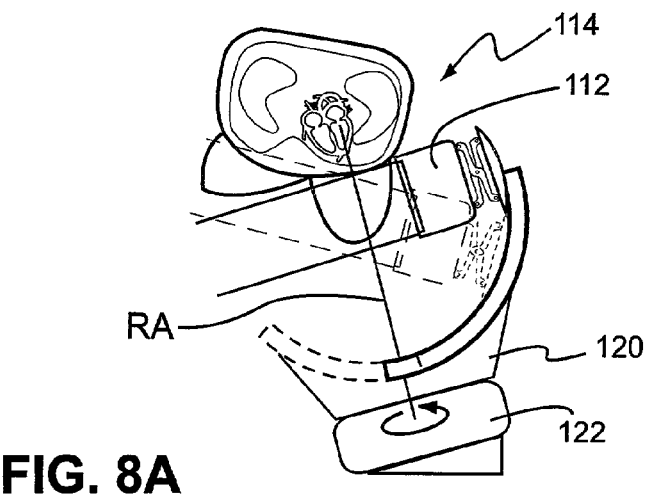
FIG. 8A is a schematic illustration of the field of views that can view axillary involvement at some projection angles.

FIG. 8A illustrates the fields of view (FOVs) using tilted orbit acquisitions that can view the breast and some axillary node involvement at some projection angles. Note that when the camera is perpendicular to the RA, however, the field of view (FOV) directly views the heart whose signal could overwhelm the smaller breast lesion signal. By rotating the camera through $\theta$ at a fixed angle about the RA, at 45° in absolute degrees relative to the RA in FIG. 8B and at 30° in absolute degrees relative to the RA in FIG. 8C, the camera will image the breast and some axillary node involvement while minimizing scattered and primary unscattered cardiac and hepatic contamination.

Figure 8B:
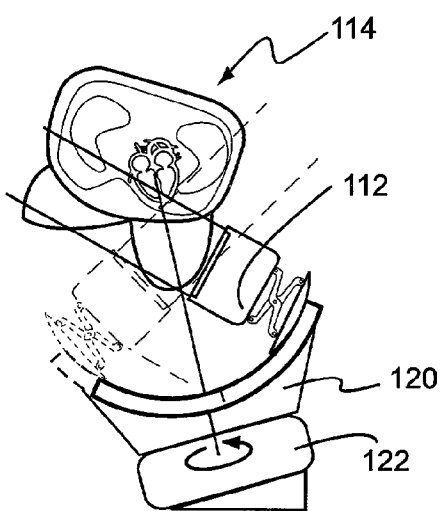
FIG. 8B is a schematic illustration of the imaging device rotating at a fixed angle of about 45° in absolute degrees polar angle relative to the Rotation Axis (RA) to image the breast alone with some axillary involvement.
Figure 8C:
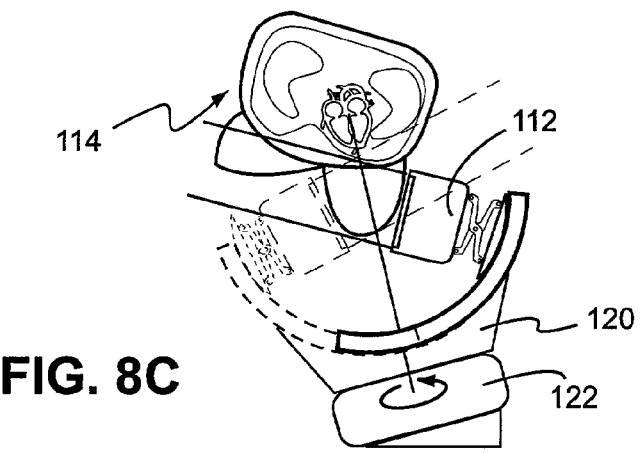
FIG. 8C is a schematic illustration of the imaging device rotating at a fixed angle of about 30° in absolute degrees polar angle relative to the rotation axis (RA) to image the breast and axillary involvement.

As illustrated in FIGS. 8A-C, the entire system platform can be titled to some appropriate angle, turned 90 degrees onto a side, or even inverted, to facilitate viewing of the particular organ or body part of interest.

Figure 9A:
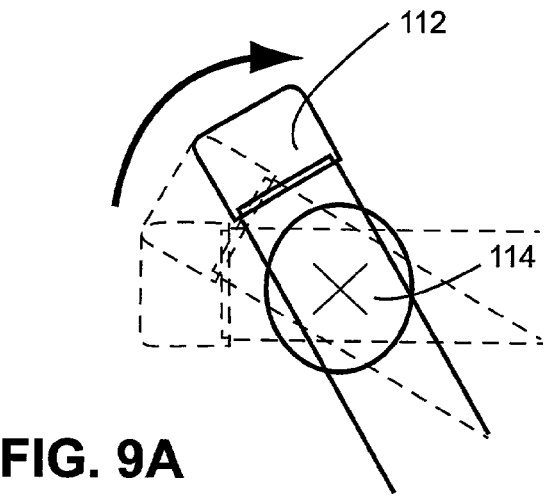
FIG. 9A is a schematic plan view illustrating a single photon camera at various angular views about the rotation axis (RA) for a small camera field of view or large breast size with respect to the camera field of view.
Figure 9B:
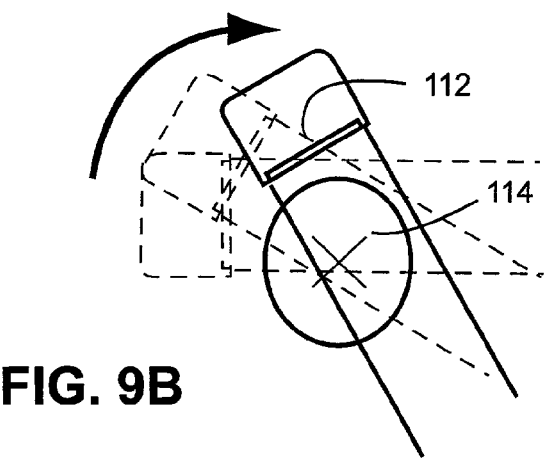
FIG. 9B is a schematic plan view illustrating a single photon camera as in FIG. 9A, but laterally shifted by L.
Figure 9C:
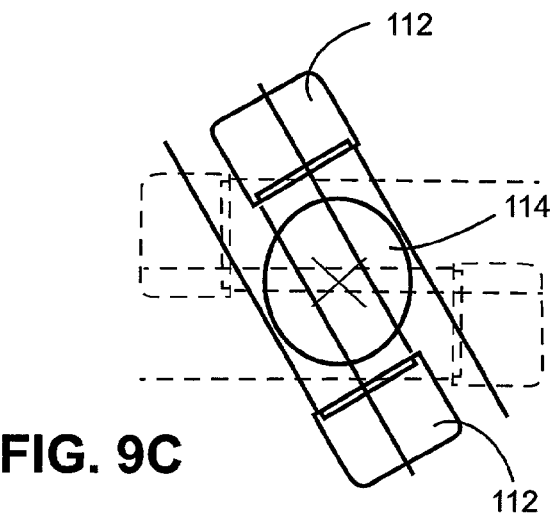
FIG. 9C is a schematic plan view illustrating a single photon camera as in FIG. 9B, but with two sets of conjugate views filling in the truncated part of the breast.

Various compact cameras under development may have smaller FOVs than necessary for dedicated breast SPECT or PET applications, and thus may not be able to view the entire breast FOV at a single projection angle. Furthermore, even larger area (20 cm) compact cameras may not be able to completely image a single breast and extended chest or axillary tissue that is simply larger than the camera's FOV. For example, given a small camera FOV or large breast size with respect to the camera FOV, a centered camera may truncate the edges of the breast tissue at some coronal levels. This will lead to incomplete data at those locations, and while only at the edges, can nevertheless detrimentally affect data within the volume of the breast. Three views are shown in FIG. 9A, in which, at each view, some part of the edges of the breast are truncated. Without increasing the physical camera size, which can be both labor intensive and quite costly for these miniaturized yet high performance components, by simply shifting the camera's centerline off-center on the dual-jack stage, as illustrated in FIG. 9B, only part of an edge will be truncated at some views, but with conjugate viewing as shown in FIG. 9C, will be 'filled in.' This shift technique requires a 360° camera orbit about the RA for SPECT, but only 180° may be sufficient for PET, so that the entire volume can be sufficiently sampled to accurately reconstruct the emission activity distribution. There is no increase in the camera's overall sensitivity since the physical FOV is not increased, but truncation of the edges of the breast image projections at any or all views are avoided by the use of intentional biased truncation only between conjugate views. A similar approach has been implemented with transmission fan beam imaging as a means to increase the effective camera FOV and avoid truncation of the torso, so that accurate attenuation maps could easily and reliably be acquired and used for accurate quantification of SPECT data. This approach can be utilized for any collimator configuration, provided there is overlap of some rays near the COR of the system.

Figure 10A:
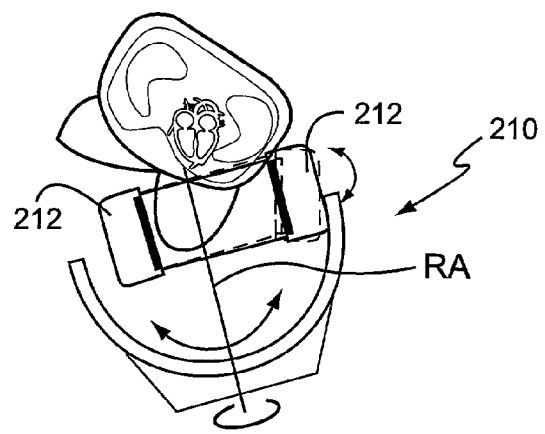
FIG. 10A is a schematic transverse view of a gantry system embodying the invention using the PET concept for the ASETT geometry with each detector mounted near an end of an extended cradle.
Figure 10B:
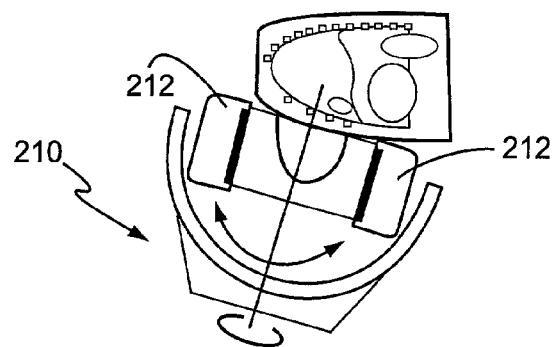
FIG. 10B is a schematic sagittal view of a gantry system embodying the invention using the PET concept for the ASETT geometry with each detector mounted near an end of an extended cradle.

The beneficial results from dedicated breast PET are as yet debatable, as discussed above. Nevertheless, its implementation to this breast imaging paradigm may prove useful. An example of a gantry capable of supporting a pair of coincident detectors is shown in FIGS. 10A-10B.

Figure 10C:
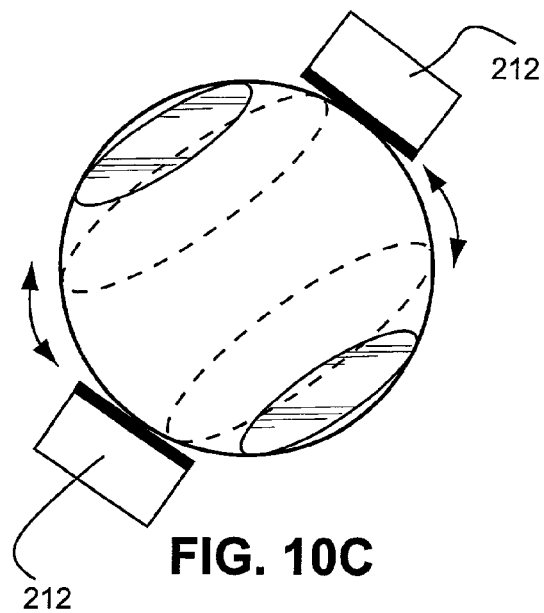
FIG. 10C is a schematic illustration of the region that can be imaged with an imaging device gantry system of the type illustrated in FIGS. 10A-B.

The primary requirement for PET is that there always be two detectors 212 and that they be in electronic coincidence. While the 90° cradle currently proposed will need additional structures to define a gantry 210 suitable to support the coincident detectors, these structures are straightforward to design, and their only requirement is that they also be able to hold remotely adjustable jack mounts to change the ROR, similar to the dual jacks 118 described above with reference to the single camera gantry 110. Use of smaller ROR goniometers to adjust individual camera tilt is also possible to account for physical hindrances, as shown in phantom in FIG. 10A. Note that the limits of the FOV change slightly with the different tilt of one camera. Also note that at some positions relative to the patient, the necessary physical requirements indicate that the detector pair may have to be at different radial distances (RORs) with a given projection viewing angle in order to avoid contact with the patient or support bed, and also to image the axillae. While this may cause changes in system sensitivity, this does not affect spatial or energy resolutions, especially for coplanar or otherwise similar detector plates. Note that these detector plates could additionally be made curved rather than parallel. The solid angle that is possible with the gantry is approximately 2pi, and would resemble a symmetrically truncated sphere of possible orbits, as shown in FIG. 10C.

Using the redesigned gantry 210 to accommodate two cameras means that two SPECT-type cameras 112 could easily be used there instead of the PET devices 212 (recall, that the SPECT cameras depend on a physical collimator to help determine the line-of-sight of the radiation while PET cameras utilize electronic collimation between two opposed detectors; the fundamental camera characteristics are otherwise identical). To further account for any physical hindrances for PET or dual camera SPECT, either or both detectors could utilize an additional angular degree-of-freedom (e.g. a smaller ROR goniometer between the camera and BGM200-type goniometer).

X-ray tomography of the breast is seeing a resurgence of interest, and prototype cameras utilize cone-beam acquisition geometries to exploit the 2-dimensionally diverging nature of the x-ray beam along with the large active surface of the digital flat-panel detectors.

Figure 11A:
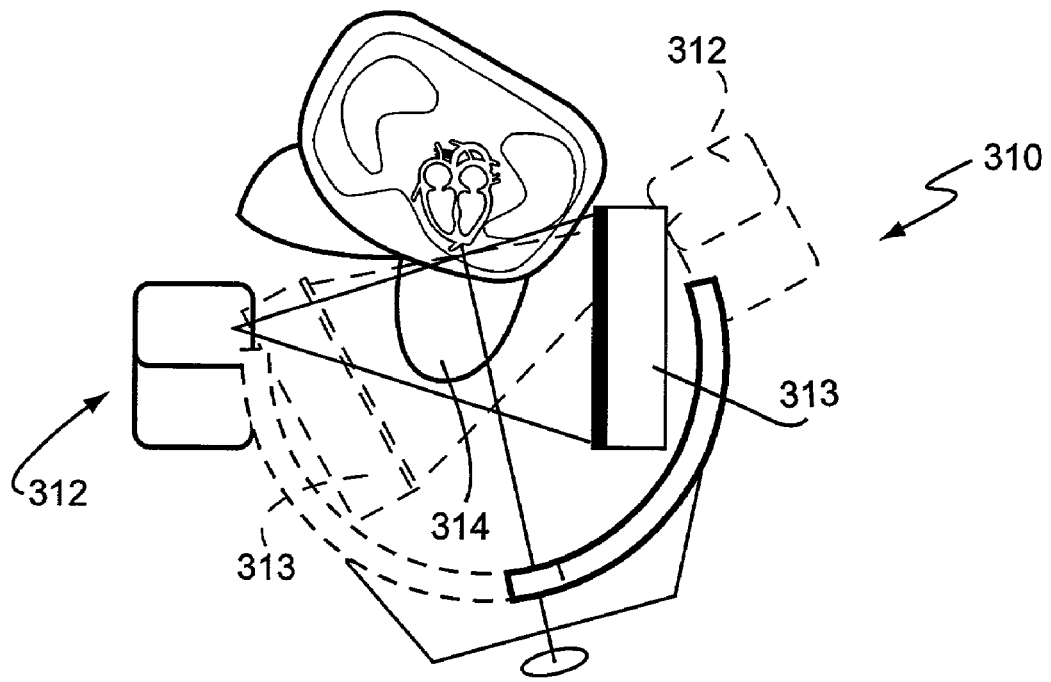
FIG. 11A is schematic transverse elevational view of an x-ray CT assembly mounted alone on the image device gantry system of the invention, or perpendicular to the emission detector(s)
Figure 11B:
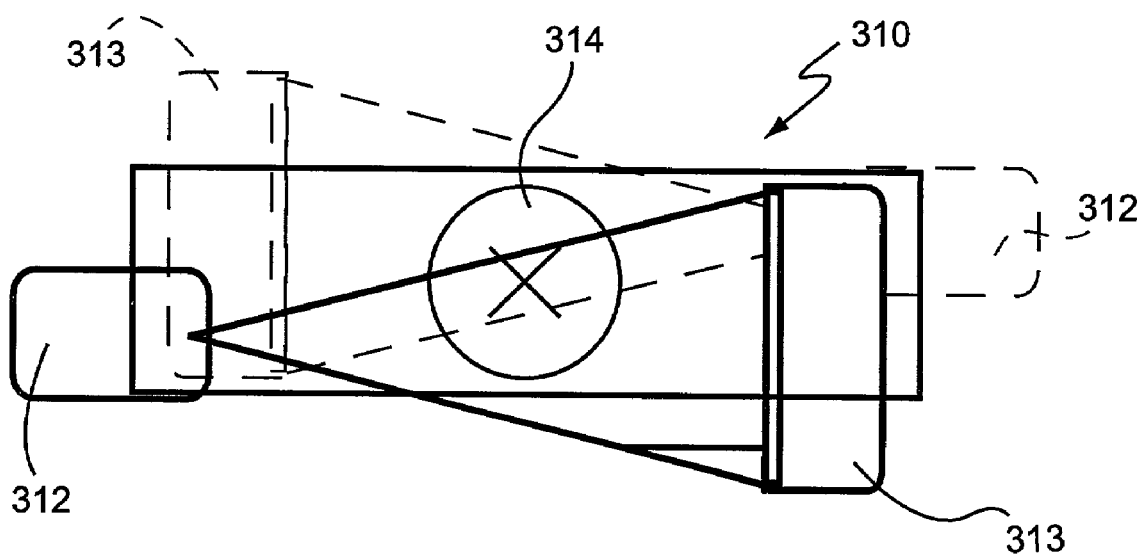
FIG. 11B is a schematic plan view of the x-ray CT assembly of FIG. 11A shifted laterally as in FIGS. 9B and 9C.

FIGS. 11A and 11B are transverse and plan views of an x-ray CT concept mounted on the ASETT gantry system of the invention, schematically shown at 310 in this embodiment. For both figures, the x-ray source 312 and detector 313 are shown in solid and in phantom to represent two conjugate, or 180° opposing projection views. Both views are necessary to completely sample the object space, while simultaneously providing lower overall exposure to the object of interest, such as a target breast 314. The source and detector may need to be backed slightly farther away than the emission systems from the breast 314 in order to ensure sufficient data collection at the nipple and axillae. Distance effects in transmission CT do not affect the spatial response in the imaged FOV as with emission tomography, so this increased distance is not problematic. In fact, this increased distance helps minimize scattered radiation at the detector. As can be seen, only part of the breast cross section is irradiated in either view such that the center-line between the source and detector is moved away from center (this can be variable and is not optimized in this drawing) which increases the effective FOV of the system (outer borders of the solid and phantom fields). With further reference to FIG. 11A, note that the center-line or central axis of the cone-beam geometry is not perpendicular to the azimuthal rotation axis (RA) in FIG. 11A, so that one edge of the pyramidal cone-beam flux nearly completely overlaps for conjugate viewing positions. This advantageously maximizes the imaged volume of the pendant breast and axillary region. The principle of laterally shifting (L) the camera(s) can be applied to the SPECT or PET emission imaging systems to increase their relative FOVs with their various collimation schemes, as described above with reference to FIGS. 9A-9C. Note also that when placed on the flexible ASETT gantry system, the dual unit source and detector can tilt as needed, similar to the PET system (FIGS. 10A-10B).

Figure 12A:
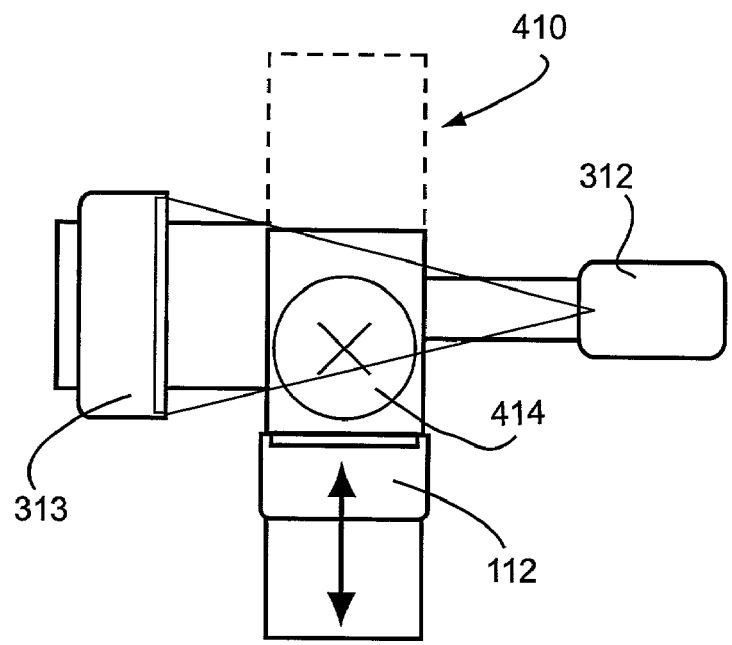
FIG. 12A is a schematic plan view of an orthogonally oriented SPECT emission and x-ray transmission imaging systems on a combined gantry system.
Figure 12B:
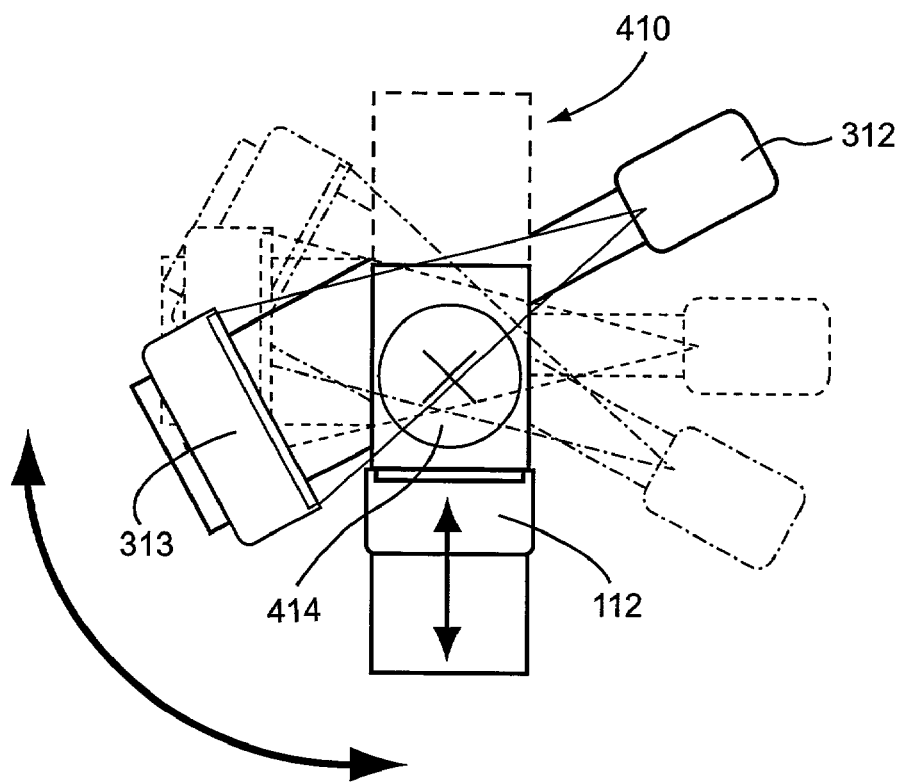
FIG. 12B is a schematic plan view similar to FIG. 12A, showing the x-ray source and detector located at various fixed angles relative to the single photon camera, with the entire system mounted for rotation.
Figure 13A:
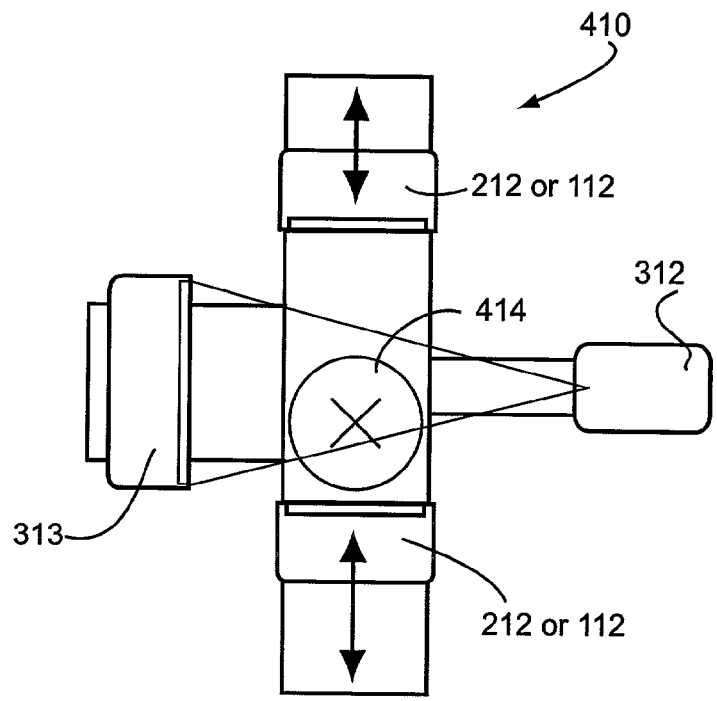
FIG. 13A is a schematic plan view of an orthogonally oriented PET emission and x-ray transmission imaging systems on a combined gantry system.
Figure 13B:
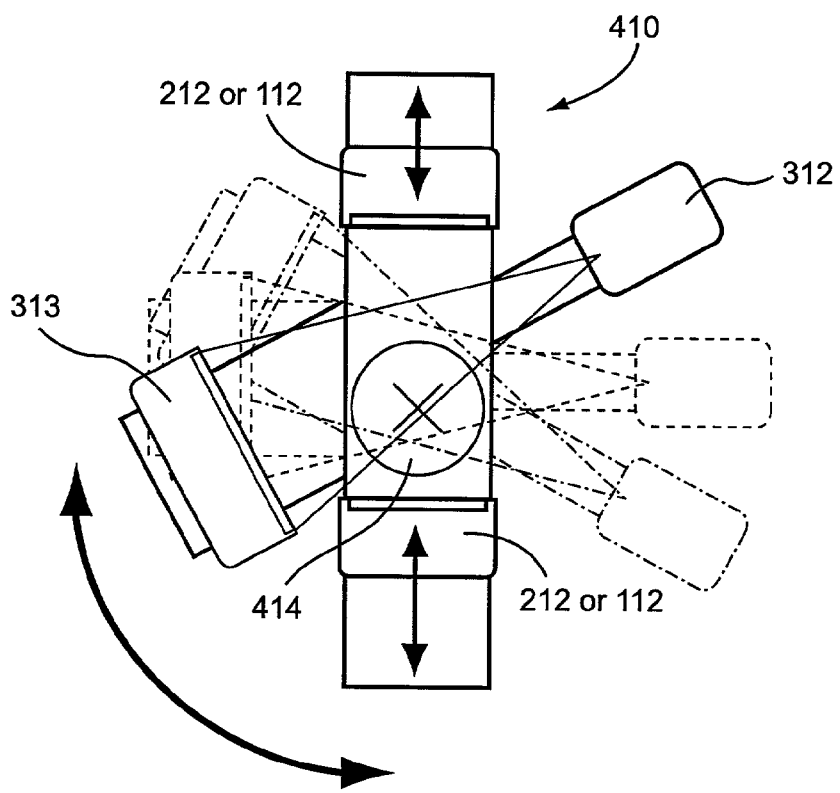
FIG. 13B is a schematic plan view similar to FIG. 13A, showing the x-ray source and detector located at various fixed angles relative to the PET camera, with the entire system mounted for rotation.

FIGS. 12A and 13A are schematic plan views of the orthogonally oriented SPECT 112 and PET 212 emission and x-ray 312,313 transmission imaging systems on a combined gantry system 410. The 'X' within the breast 414 designates the axis-of-rotation; note that the central ray of the x-ray CT system 312,313 does not intersect the AOR. In these exemplary embodiments, the x-ray source (e.g. from a Lorad M-IV) and the x-ray detector (e.g. Varian Paxscan 2520 which has a 25×20 cm FOV) are disposed on a fixed gantry, but a gantry according to the invention can be placed underneath the emission detector. Note also that in order to accommodate the short focal length cone-beam x-ray system, as well as help avoid physical interference with the torso, the PET detectors 212 may have different or variable RORs at different projection viewing angles. The x-ray CT and SPECT or PET systems are shown orthogonally oriented in FIGS. 12A and 13A. However, the x-ray source and detector could be located at various fixed, unique angles relative to the Single Photon or PET camera, respectively, as shown in FIGS. 12B and 13B, and the entire system disposed for rotation. In fact, some preliminary measurements with an x-ray source suggest that a non-orthogonal orientation may be better.

The concepts of the orthogonally oriented SPECT or PET emission systems along with x-ray transmission imaging systems on a combined gantry is not new, but its application to breast imaging, and especially with the novel implementation described herein are completely new approaches. Other systems have typically utilized larger area clinical gamma camera detectors which physically limit the ability to bring the detector into close proximity with the breast, and the x-ray CT systems they are combined with are also better suited for whole body imaging and not dedicated to a specific organ.

The approaches proposed here differ from other approaches for three primary reasons: (1) this approach can utilize the x-ray source and detector individually mounted onto the flexible gantry; furthermore, (2) by utilizing an offset cone-beam geometry (FIGS. 11A and 11B) two factors are enhanced compared with traditional cone-beam imaging: (a) incomplete sampling at the extent of the conebeam field may be reduced yielding more accurate spatial recovery of small objects near the edge of the field-of-view with cone-beam reconstruction techniques (this has been shown with fan-beam transmission imaging in SPECT, and the extended principle here obtains), although this approach does require a full 360° rotation acquisition to obtain conjugate views of the object-of-interest rather than only 180° needed in principle; (b) by only irradiating a portion of the object-of-interest, in this case the breast, the overall exposure and dose to the breast with this CT approach may be substantially reduced since the entire volume of the breast is not irradiated for the full 360° source-detector orbit; finally, (3) by mounting the x-ray CT device orthogonal (or near orthogonal as shown in FIGS. 12B and 13B) to the emission imaging system (SPECT or PET) on a fixed gantry (or a flexible gantry underneath or above the emission system) dual modality imaging yielding perfectly coregistered structural and functional information obtained simultaneously is possible (FIGS. 12A, 12B, 13A, and 13B). Having the structural information also facilitates both attenuation correction of the emission SPECT or PET images and also scatter modeling to improve image quantification based on knowledge of the presence and locations of non-native structures such as breast enhancements, overall objective evaluation of the more noisy SPECT or PET data with the structural information, etc.

Example

A novel ASETT system including the LumaGEM™ compact gamma camera for tomographic emission imaging of the breast was designed and built, and the system evaluated by Monte Carlo simulations and measurements of phantoms with breast lesions of various sizes and locations. Additional radioactivity was included in the anthropomorphic torso phantom's cardiac and liver inserts to simulate the large backgrounds anticipated with clinical imaging of $^{99m}$Tc-compounds used to evaluate breast disease.

Simulations: Initial Monte Carlo simulations (MCs) of analytical phantoms were performed with 140 keV gamma rays to determine the feasibility of utilizing a compact system for emission imaging of the breast with the ASETT dedicated, compact tomographic system. An available ~950 ml ellipsoidal breast phantom (12 cm length, 13.5 short and 15 cm long elliptical diameters) with centrally located 1 cm diameter lesion was simulated with 6:1 lesion to breast background ratio. Based on using available clinical and compact gamma cameras, this simulated phantom was tomographically imaged on a vertical axis-of-rotation (VAOR) at various radii-of-rotation (RORs) with different camera and collimator characteristics and without tilt.

Emission Prototype: An ASETT system was constructed utilizing a commercially available compact gamma camera with 2×2×6 mm quantized NaI(T1) scintillators coupled to position sensitive PMTs. The camera was mounted on a support with 2 to >8 cm variable ROR. This unit is further mounted on a limited angle goniometric cradle with polar motion, and in turn mounted on a rotation stage (azimuthal motion) capable of indefinite VAOR about the rotation axis (RA). The combination of radial, polar and azimuthal motions can achieve nearly any contiguous orbit on inverted hemispheres with >2 pi solid angle.

Emission Measurements (A) Initial measurements with Tc-99m (140 keV) to evaluate the system included acquisitions with camera polar tilt angles from about 0 to 45 degrees about the RA without lateral camera shifting and full 360° azimuthal acquisition. It is anticipated that physical limitations will occur with patient imaging due to hindrance from the support bed, sheets, IV lines and other potential physical encumbrances. The versatility of the ASETT gantry facilitates adaptive positioning in the pendulous breast reference frame for the given situation.

Tomographic measurements were compared with uncompressed planar measurements of 0.6 and 1.0 cm diameter fillable lesions with <11:1 lesion uptake ratios of Tc-99m in a breast phantom attached to an anthropomorphic torso phantom with lesion to breast-and-body to cardiac to liver activity ratios of 11:1:19:19. Various photopeak energy windows of 10%, 15%, 20% and 30% FWHM were obtained along with a 35% scatter window below the 15% photopeak window from the list mode data. Projections with all photopeak window and simple camera tilt conditions were reconstructed with an ordered subsets expectation maximization (OSEM) algorithm capable of reconstructing arbitrary tomographic orbits (linear reconstruction algorithms, while as yet unavailable for the complex orbits possible with the image acquisition system, may also be possible to be used).

(B) Additional tomographic measurements were made with a laterally shifted camera with fixed polar tilt angles from 0° to 30° similar to the initial experiments, and also more complex orbits with dynamically varying polar tilt angles from 0° up to 60°, both with full 360° azimuthal system rotation. The complex orbits employing dynamic polar positioning were designed to satisfy Orlov sufficiency sampling criteria and also avoid physical hindrances expected in the clinical scenarios; the sufficiency sampling was first experimentally validated with cold disk and rod-resolution phantoms, then used on the anthropomorphic phantoms. The orbits can be described as follows: (a) tilted parallel beam (with fixed polar angles from 0° to 30° for fall 360° azimuthal acquisition); (b) circle plus arc (similar to (a) tilted parallel beam acquisition along with an additional polar arc which has twice the maximum polar angular displacement as camera tilt); (c) circle plus symmetric arcs (similar to (a) tilted parallel beam but with two 180° opposing additional arcs, each having angular displacement equal to the camera tilt angle); (d) spiral plus arcs (two arcs from 0° to 30° similar to those in (c) with a changing polar tilt angle with advancing azimuth, with paths connecting the zenith of one arc with the nadir of the other, thus forming a spiral); and (e) incomplete circular orbit (0° to 90° polar orbit at fixed azimuth, then 180° azimuthal rotation, then 90° to 0° polar orbit, in fall, resembling a semicircle when viewed from planar or lateral angle).

The complex tomographic imaging used the same lesions and anthropomorphic torso components with lower activity concentration ratios for the lesions to breast-and-body to cardiac to liver activity ratios of 7:1:13:13, compared with the former initial experiments. A 15% window about the 140 keV 99mTc photopeak was used for all measurements, and all data were reconstructed with the OSEM algorithm.

Transmission Prototypes and Measurements: A generic transmission system was constructed utilizing the same emission gamma camera with or without a collimator on the front-end. (A) In the first implementation, a planar collimated emission source was mounted on the goniometer gantry at a large enough distance from the collimated gamma camera so as to allow the anthropomorphic breast phantom to be freely suspended in the shifted camera's FOV, similar to FIGS. 9B and 9C but with a source opposite the camera. (B) In the second implementation, a point source was mounted away from and at the outer edge of the uncollimated gamma camera so as to allow the breast to fit in the truncated FOV of the shifted camera, similar to that in FIG. 11B. This geometry represents a truncated or shifted cone beam geometry.

Results (Simulation): Reconstructed MCs of simulated data yielded >7 fold increase in ASETT-to-planar image contrast, and simulated dedicated systems performed equal to or >50% better than a dedicated large area gamma camera.

Results (Emission A): As iteration number increased for the tomographically measured data at all polar angles, contrasts increased while signal-to-noise ratios (SNRs) decreased in the expected way with OSEM reconstruction. Two iterations yielded a good trade-off between contrast improvement and continued SNR degradation. The reconstructed ASETT data yielded SNRs that were >9 times better than the planar data with or without scatter correction. There was up to a factor of ~2.5 increase in total primary and scatter contamination in the photopeak window with increasing tilt angle from 15 to 45 degrees, consistent with more direct line-of-sight of myocardial and liver activity with increased camera polar angle.

Results (Emission B): Camera shift eliminated truncation artifacts in reconstructions, and overall, complex orbits demonstrated fewer contaminations from torso backgrounds than data collected with the more simple orbits. All complex orbits could recover the uniform cold and hot disks with a high degree of uniformity, and up to the maximum polar angles, the 3.1 mm rods could be easily distinguished in the reconstructions for data acquired with these complex orbits. Lesion contrasts were up to 6 times better and SNRs were 2 times better than similar planar measurements of the same phantoms. Lesion contrast (range 3.5-7.3) and SNR (range 10.5-23.3) values for all orbits were nearly similar (for contrast ±25% variation, for SNR±20% variation), with the circle plus symmetric arcs having the highest (outlying) overall values.

Results (Transmission): The transmission projections and reconstructed transmission maps illustrated the feasibility of acquiring untruncated transmission data with both geometries. Specifically, even with the 4 times smaller FOV of the LumaGEM™ camera than the anticipated larger FOV x-ray device, untruncated breast transmission data could be acquired, albeit in a limited FOV along the nipple-chest axis. The larger FOV of the anticipated detector will allow larger object-to-image distance leading to less image scatter, and larger overall FOV of the breast and axillary region. Furthermore, the attenuation coefficients of the reconstructed (A) parallel beam and (B) cone beam transmission measurements were 0.150 cm−1 and 0.114 cm−1, respectively, which compare favorably with the narrow beam attenuation value of water (in the filled breast) at 140 keV of 0.152 cm−1; the cone beam values are expected to improve when appropriate collimation and reconstruction is used with this test system. Furthermore, with attenuation correction of the reconstructed 0° tilted parallel beam emission data, signal intensities increased by a factor of >2 compared with uncorrected reconstructions, and >15 times compared with lesion intensities obtained from planar measurements. It is important to note that the limited cone beam FOV in this transmission configuration did not truncate the data and required comparably lower source strength to the parallel beam configuration, indicating that the expected x-ray fluxes in the proposed system (FIGS. 11 and 12) should yield low noise in the reconstructed images.

Conclusions: Combined with an appropriate iterative reconstruction algorithm, the simulated and measured tomographic results outperformed currently accepted planar imaging by over an order of magnitude in terms of improved signal-to-noise ratios and lesion contrasts of small and larger (0.6 cm and 1.0 cm diameter, respectively) lesions. The application of scatter correction in the reconstruction further improved the results, especially for the larger lesion. With application of attenuation correction, as well as modeling of spatial response function and Poisson noise in the data, quantitative information could be extracted from the data. Having fully quantitative data is significant for several reasons. (1) The ability to determine uptake values which can be monitored over time, especially as a patient receives any therapies and treatment, can help guide the course of therapy. (2) Correlation of this functional imaging information with ancillary imaging studies, e.g. with x-ray CT or MRI can help determine the viability or grade of the lesions; for example, while a high resolution MRI scan can provide information about and the locations of various lesions, correlation with functional information obtained from the volumetric ASETT approach can help determine their activity, which may be an indicator of malignancy. This functional-structural correlation can also be used to guide surgery, in that radial dissection or mastectomy can be precluded knowing that, for example, only 1 in 5 lesions seen in MRI may exhibit radiopharmaceutical uptake. (3) The functional information could thus potentially be used to help grade lesions. Other applications are certainly possible.

Thus, combined with a high performance, compact gamma camera, this new, ultra-compact, high performance dedicated ASETT imaging system can provide valuable, fully 3-dimensional functional information about small (<1 cm), otherwise indeterminate breast lesions as an adjunct to diagnostic mammography. Furthermore, this emission system can be combined with a novel transmission imaging system on the same gantry with which to simultaneously obtain coregistered, 3-dimensional structural information about the breast.

As discussed above, the flexible single photon imaging emission system tested herein can be replaced by dual, coincident PET detectors, with each detector placed opposite the other, and both detectors attached to a modified goniometric cradle (FIGS. 10A-10C). Furthermore, a transmission imaging system utilizing single or coincident photons from nuclear medicine techniques, or an x-ray transmission system (x-ray source and digital, flat panel detector) could also be placed on this goniometric cradle and gantry system (FIGS. 11A-11B). Moreover, the transmission system can be directly placed in a more static orientation, orthogonally or nearly orthogonally, to either the single photon or coincident flexible emission system (FIGS. 12A, 12B, 13A, and 13B).

The proposed ASETT system gantry is expected to improve breast lesion imaging with compact cameras for at least two reasons. (1) It can move a camera closer to the breast over a broader angular range than conventional, large SPECT gamma cameras. Since the spatial resolution of gamma camera collimators improves markedly as the camera moves closer to an object, this provides improved spatial resolution, and potentially a transition from collimator-limited resolution to resolution determined by the detector. Hence, the use of quantized detectors with very small elements, or continuously positioning devices with very fine spatial resolution are ideal for use with this gantry system. (2) There is a broad range of angles within the total set of projection positions at which the ASETT system would primarily view the breast alone, and would not view background activity from the heart and/or liver. It is desirable, then, to use orbits within the hemisphere of physically possible orbits (FIGS. 7D, 10C) that would avoid or minimize viewing the heart and liver, but that would acquire a set of close-proximity ASETT projection data that is sufficient to reconstruct activity in (with emission tomography) or through (with transmission tomography) the breast, neighboring chest wall and axillae. Lesion visualization in the upper-outer quadrant of the breast is particularly important since >50% of breast cancers occur there.

The information obtained from 3-dimensional functional imaging, especially when combined with 3-dimensional structural images can be used to guide computer controlled biopsy or as a guide to surgical dissection. Functional imaging used to guide biopsy has been investigated, albeit with limited true 3-dimensional information.

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims. Thus, while gamma cameras, which generate images of ionizing radiation have been described in exemplary embodiments of the invention, the gantry system of the invention may be used with cameras that generate images with non-ionizing radiation, such as a visible light or infrared sensitive charge coupled device (CCD).

What is claimed is:

1. A motorized and computer controlled imaging system for generating images of a target body part suspended within an imaging area of the system, comprising:
a support having a rotation axis extending through the imaging area and at least one imaging device having an imaging device axis which passes through a first imaging device field of view, the imaging device being mounted to the support so as to be selectively movable during imaging in three dimensions, including radial movement relative to the rotation axis, rotational movement about the rotation axis, vertical movement parallel to the rotation axis, and pivoting movement about a pivot axis perpendicular to said rotation axis, whereby said imaging device can be selectively moved along a path that defines a curved 3-dimensional surface,
wherein said at least one imaging device comprises a pair of gamma cameras,
whereby said gamma cameras can be selectively moved during imaging along a 3D path that defines a curved 3-dimensional surface, to acquire data to generate a 3-dimensional image, and will, while traveling in a downward arc toward a pole of the target body part, move vertically downward and pivot to continue to face the surface of the body part being imaged.

2. An imaging system as in claim 1, wherein said pair of gamma cameras are mounted to said support so as to face in generally diametrically opposite directions for coincidence imaging.

3. An imaging system as claim 2, wherein said PET detectors can be selectively moved along a three-dimensional path that defines substantially a banded orbit.

4. An imaging system for generating images of a body part suspended within an imaging area of the system, comprising:
a support having a rotation axis extending through the imaging area and at least one imaging device having an imaging device axis which passes through a first imaging device field of view, the imaging device being mounted to the support so as to be selectively movable in three dimensions, including radial movement relative to the rotation axis, rotational movement about the rotation axis, vertical movement parallel to the rotation axis, and pivoting movement about a pivot axis perpendicular to said rotation axis, whereby said imaging device can be selectively moved along a path that defines a curved 3-dimensional surface,
wherein said imaging device comprises a gamma camera or a detector for Positron Emission Tomography (PET), and
further comprising an X-ray source and an X-ray detector disposed diametrically opposite said X-ray source, said X-ray source and X-ray detector being disposed such that a line extending from said X-ray source to said X-ray detector is disposed at an angle to said imaging device axis.

5. An imaging system as in claim 4, wherein said angle is between about 45 and 135 degrees.

6. An imaging system for generating images of a body part suspended within an imaging area of the system, comprising:
a support having a rotation axis extending through the imaging area and an imaging device having an imaging device axis which is the center axis of a field of view of the imaging device, the imaging device being mounted to the support so as to be selectively movable in three dimensions, including radial movement relative to the rotation axis, rotational movement about the rotation axis, vertical movement parallel to the rotation axis, and pivoting movement about a pivot axis perpendicular to said rotation axis, whereby said imaging device can be selectively moved along a path that defines a curved 3-dimensional surface,
wherein said imaging device axis is laterally offset from said rotation axis so that said imaging device axis does not intersect said rotation axis and said support is mounted for rotational movement through at least about 180 degrees, whereby when the body part is greater than the imaging device field of view, an entire volume of said body part can be sufficiently sampled to accurately reconstruct the emission activity and/or object distributions.

7. An imaging system as in claim 6, wherein said support is mounted for rotation through and including 360 degrees.

8. An imaging system as in claim 6, wherein said imaging device comprises an X-ray source and X-ray detector mounted diametrically opposite one another.

9. An imaging system as in claim 8, wherein said imaging device axis is inclined with respect to said rotation axis to maximize a path of x-rays through an object disposed in said field of view.

10. A gantry for dedicated 3-dimensional tomographic imaging of a target body part, comprising:
- an imaging device support assembly including an imaging device support and a motorized and computer controlled translation assembly for displacing said imaging device support relative to a said body part;
- a rotary support assembly for rotating said imaging device support assembly about a rotary axis thereof, for displacing said imaging device support about a periphery of said body part, at a radius of rotation determined at least in part by said imaging device support assembly; and
- at least one imaging device pivotally mounted to said imaging device support,
- wherein said imaging device is selectively pivoted at said pivot mounting with respect to said imaging device support during imaging, so that a face of said imaging device can be selectively disposed generally parallel to a surface of the body part,
- wherein at least one of said imaging device support assembly and said rotary support assembly is height adjustable during imaging to determine a spacing of the imaging device from said body part,
- wherein said translation assembly is configured to provide selective displacement of the imaging device support, during imaging, through an angle ϕ about a pivot axis perpendicular to said rotation axis, and
- wherein at least one of said imaging device support and said translation assembly is configured to selectively radially displace the imaging device mounted thereto, during imaging, relative to the rotation axis,
- whereby said imaging device can be selectively moved during imaging along a 3D path that defines a curved 3-dimensional surfaces, to acquire data to generate a 3-dimensional image, and will, while traveling in a downward arc toward a pole of the target body part, move vertically downward and Divot to continue to face the surface of the body part being imaged.

11. A gantry as in claim 10, wherein said translation assembly displaces said imaging device support radially of said rotary axis.

12. A gantry as in claim 10, wherein said imaging device support comprises an elevation assembly for selectively displacing an imaging device mounted thereto radially with respect to said pivot axis for selectively changing a radius of rotation of the imaging device or for following a contour of the surface of the body part.

13. A gantry as in claim 10, wherein said translation assembly comprises a cradle system for providing at least ±45° angular motion and wherein said imaging device support is mounted to said cradle system, whereby the imaging device mounted to said imaging device support may be selectively displaced through an angle of at least about 90°.

14. A gantry as in claim 13, wherein said imaging device support comprises a platform and an elevation assembly for selectively displacing said platform from said cradle, for selectively changing a radius of rotation of the imaging device or for following a contour of the surface of the body part.

15. A gantry as in claim 10, wherein said imaging device comprises a SPECT camera.

16. A gantry as in claim 10, wherein an axis of said imaging device axis is laterally offset from said rotation axis and said rotary support assembly is mounted for rotational movement through at least about 180 degrees.

17. A gantry as in claim 10, comprising first and second imaging devices mounted to said imaging device support assembly for being disposed on generally diametrically opposite sides of said body part.

18. A gantry as in claim 10, wherein said translation assembly comprises a cradle system and further comprising a pair of detectors for Positron Emission Tomography (PET), one respectively mounted adjacent each end of said cradle.

19. A gantry as claim 10, wherein said imaging device can be selectively moved along a three-dimensional path that defines substantially a banded orbit.

20. A gantry as claim 10, wherein said imaging device can be selectively moved along a path that defines substantially a hemisphere.

21. A gantry for dedicated 3-dimensional tomographic imaging of a body part, comprising:
- an imaging device support assembly including an imaging device support and a translation assembly for displacing said imaging device support relative to a said body part;
- a rotary support assembly for rotating said imaging device support assembly about a rotary axis thereof, for displacing said imaging device support about a periphery of said body part, at a radius of rotation determined at least in part by said imaging device support assembly;
- an imaging device mounted to said imaging device support, wherein said imaging device comprises a gamma camera or a detector for Positron Emission Tomography (PET); and
- an X-ray source and an X-ray detector disposed diametrically opposite said X-ray source, said X-ray source and X-ray detector being disposed such that a line extending from said X-ray source to said X-ray detector is disposed at an angle to an axis of said imaging device,
- wherein at least one of said imaging device support assembly and said rotary support assembly is height adjustable to determine a spacing of an imaging device mounted to said imaging device support from said body part,
- wherein said imaging device support assembly is configured to provide selective displacement of an imaging device mounted thereto through an angle ϕ about a pivot axis perpendicular to said rotation axis, and
- wherein at least one of said imaging device support and said translation assembly is configured to selectively radially displace an imaging device mounted thereto relative to the rotation axis.

22. A gantry as in claim 21, wherein said angle is between about 45 and 135 degrees.

23. A method for three-dimensional tomographic imaging of a target body part of a patient comprising:
- positioning at least one imaging device adjacent a surface of the target body part; and
- using a motorized and computer controlled imaging device gantry system, selectively displacing said imaging device, during imaging, in a direction radial to a central axis of said target body part, in a rotary direction about a rotational axis along at least a part of a circumferential surface of the target body part, through a pivot angle about a pivot axis transverse to said rotational axis, and vertically with respect to the patient so that during imaging said imaging device follows an approximate three-dimensional surface of at least a portion of said target body part by travelling along a 3D path and will, while traveling in a downward arc toward a pole of the target body part, move vertically downward and pivot to continue to face the surface of the body part being imaged.

24. A method as in claim 23, wherein said step of selectively displacing includes incrementally rotating the imaging device about the target body part such that measurements of the target body part are taken at a number of angular orientations.

25. A method as in claim 23, including mounting said imaging device so that an axis of a field of view thereof is laterally offset from said rotation axis and selectively rotating said imaging device through at least about 180 degrees.

26. A method as in claim 25, wherein said imaging device comprises an X-ray imaging system and further including mounting said imaging device so that said field of view axis thereof is inclined with respect to said rotation axis to maximize a path of x-rays through the target body part disposed in said field of view.

27. A method as in claim 23, wherein said imaging device comprises a SPECT camera.

28. A method as in claim 23, wherein said at least one imaging device comprises a pair of detectors for Positron Emission Tomography (PET).

29. A method as in claim 23, further comprising guiding a biopsy or tissue extraction device to a target region within the target body part and obtaining a tissue sample.

30. A method as in claim 23, further comprising acquiring data from said imaging device as said imaging device substantially continuously follows said approximate three-dimensional surface, whereby a three-dimensional image can be generated.

31. A method as in claim 30, wherein said data is acquired substantially without compression of the target body part.

32. A method as in claim 30, wherein said data is acquired in list mode.

33. A method as in claim 23, wherein the target body part is a breast, and further comprising placing and supporting the patient in a prone position with the target breast depending downwardly from the supported patient.

34. A method as in claim 33, further comprising acquiring data from said imaging device as said imaging device substantially continuously follows said approximate three-dimensional surface, whereby a three-dimensional image can be generated.

35. A method as in claim 34, wherein said data is acquired substantially without compression of the pendant breast.

36. A method as in claim 34, wherein said data is acquired in list mode.

* * * * *